(12) United States Patent
Follows et al.

(10) Patent No.: US 9,839,284 B2
(45) Date of Patent: Dec. 12, 2017

(54) CLEANING APPLIANCE

(71) Applicant: Dyson Technology Limited, Wiltshire (GB)

(72) Inventors: Thomas James Dunning Follows, Swindon (GB); William John Bex-Russell, Horsham (GB); Timothy Nicholas Stickney, Gloucester (GB); Stephen Benjamin Courtney, Bath (GB); Peter David Gammack, Swindon (GB)

(73) Assignee: Dyson Technology Limited, Malmesbury, Wiltshire (GB)

( * ) Notice: Subject to any disclaimer, the term of this patent is extended or adjusted under 35 U.S.C. 154(b) by 0 days.

(21) Appl. No.: 15/152,116

(22) Filed: May 11, 2016

(65) Prior Publication Data

US 2016/0331114 A1  Nov. 17, 2016

(30) Foreign Application Priority Data

May 15, 2015 (GB) .................................. 1508366.0

(51) Int. Cl.
| | |
|---|---|
| *A46B 11/04* | (2006.01) |
| *A46B 13/04* | (2006.01) |
| *A61C 17/02* | (2006.01) |
| *A61C 17/22* | (2006.01) |
| *A61C 17/36* | (2006.01) |

(Continued)

(52) U.S. Cl.
CPC ............ *A46B 13/04* (2013.01); *A46B 5/0095* (2013.01); *A46B 7/08* (2013.01); *A46B 9/04* (2013.01); *A61C 17/02* (2013.01); *A61C 17/0202* (2013.01); *A61C 17/221* (2013.01); *A61C 17/222* (2013.01); *A61C 17/227* (2013.01); *A61C 17/36* (2013.01); *A61C 17/40* (2013.01)

(58) Field of Classification Search
CPC ...... A61C 17/16; A61C 17/028; A46B 11/002; A46B 11/0065; A46B 2200/108
See application file for complete search history.

(56) References Cited

U.S. PATENT DOCUMENTS

| | | | |
|---|---|---|---|
| 2,766,472 | A | 10/1956 | Durrett |
| 3,195,537 | A | 7/1965 | Blasi |

(Continued)

FOREIGN PATENT DOCUMENTS

| | | |
|---|---|---|
| CN | 105943179 | 9/2016 |
| CN | 106109041 | 11/2016 |

(Continued)

OTHER PUBLICATIONS

International Search Report and Written Opinion dated Sep. 12, 2016, directed to International Application No. PCT/GB2016/051148; 18 pages.

(Continued)

*Primary Examiner* — Jennifer C Chiang
(74) *Attorney, Agent, or Firm* — Morrison & Foerster LLP

(57) ABSTRACT

A dental cleaning appliance includes a handle, and a cleaning tool detachably connected to the handle. The cleaning tool includes a nozzle for delivering a burst of working fluid to the teeth of a user, a stem extending between the handle and the nozzle, and a fluid reservoir for storing working fluid. The fluid reservoir is connected to, and extends around, the stem.

35 Claims, 24 Drawing Sheets

(51) Int. Cl.
*A46B 5/00* (2006.01)
*A46B 7/08* (2006.01)
*A46B 9/04* (2006.01)
*A61C 17/40* (2006.01)

(56) References Cited

U.S. PATENT DOCUMENTS

| | | | |
|---|---|---|---|
| 3,235,897 | A | 2/1966 | Fortenberry |
| 4,961,698 | A | 10/1990 | Vlock |
| 4,978,297 | A | 12/1990 | Vlock |
| 5,218,956 | A | 6/1993 | Handler et al. |
| 5,393,153 | A | 2/1995 | Bouthillier et al. |
| 6,155,824 | A | 12/2000 | Kamen et al. |
| 6,164,967 | A | 12/2000 | Sale et al. |
| 6,402,410 | B1 | 6/2002 | Hall et al. |
| 6,536,979 | B1 | 3/2003 | Kenny et al. |
| 6,599,126 | B1 | 7/2003 | Sale et al. |
| 6,689,078 | B1 | 2/2004 | Rehkemper et al. |
| 6,739,782 | B1 | 5/2004 | Rehkemper et al. |
| 6,766,549 | B2 * | 7/2004 | Klupt .............. A61C 17/36 15/22.1 |
| 7,080,980 | B2 | 7/2006 | Klupt |
| 7,596,827 | B1 | 10/2009 | Puneet |
| 7,896,567 | B2 | 3/2011 | Burrowes |
| 8,522,384 | B2 | 9/2013 | Leung |
| 8,651,340 | B2 | 2/2014 | Lelieveld et al. |
| 9,144,298 | B2 | 9/2015 | Fattori |
| 2002/0044817 | A1 | 4/2002 | Hall et al. |
| 2002/0152565 | A1 | 10/2002 | Klupt |
| 2005/0238412 | A1 | 10/2005 | Jacobs et al. |
| 2005/0254992 | A1 | 11/2005 | Jenkins et al. |
| 2006/0292521 | A1 | 12/2006 | Hegemann |
| 2007/0039109 | A1 | 2/2007 | Nanda |
| 2007/0080240 | A1 | 4/2007 | Schuetz |
| 2008/0008979 | A1 | 1/2008 | Thomas et al. |
| 2009/0136285 | A1 | 5/2009 | Hall et al. |
| 2009/0305187 | A1 | 12/2009 | Janssen et al. |
| 2012/0183926 | A1 | 7/2012 | Shalev |
| 2012/0266396 | A1 | 10/2012 | Leung |
| 2013/0122453 | A1 | 5/2013 | Paxton et al. |
| 2014/0033034 | A1 | 1/2014 | Patel |
| 2014/0259474 | A1 | 9/2014 | Sokol et al. |
| 2015/0335144 | A1 | 11/2015 | Patel |
| 2016/0331115 | A1 | 11/2016 | Follows et al. |
| 2016/0331116 | A1 | 11/2016 | Follows et al. |

FOREIGN PATENT DOCUMENTS

| | | |
|---|---|---|
| DE | 99427 | 9/1897 |
| DE | 1632384 | 6/1971 |
| DE | 9417795 | 5/1994 |
| DE | 69021971 | 5/1996 |
| DE | 29703210 | 4/1997 |
| DE | 29807736 | 11/1998 |
| DE | 20018077 | 2/2001 |
| FR | 341238 | 8/1904 |
| FR | 2 790 383 | 9/2000 |
| GB | 2290702 | 1/1996 |
| GB | 2538300 | 11/2016 |
| GB | 2538302 | 11/2016 |
| GB | 2538304 | 11/2016 |
| JP | 10-113230 | 5/1998 |
| JP | 11-103937 | 4/1999 |
| JP | 2003-304933 | 10/2003 |
| JP | 2007-14730 | 1/2007 |
| WO | WO-90/12557 | 11/1990 |
| WO | WO-2006/134514 | 12/2006 |
| WO | WO-2008/046580 | 4/2008 |
| WO | WO-2010/055435 | 5/2010 |
| WO | WO-2011/094587 | 8/2011 |

OTHER PUBLICATIONS

Search Report dated Nov. 13, 2015, directed to GB Application No. 1508366.0; 1 page.

* cited by examiner

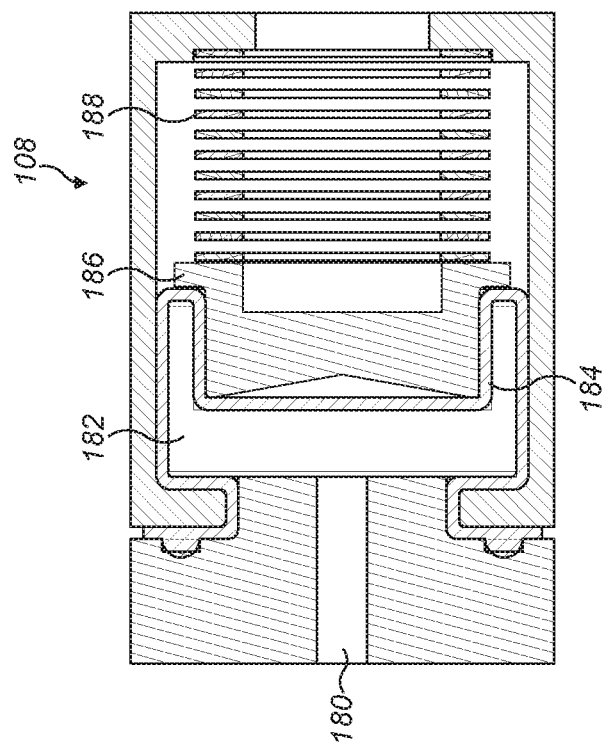
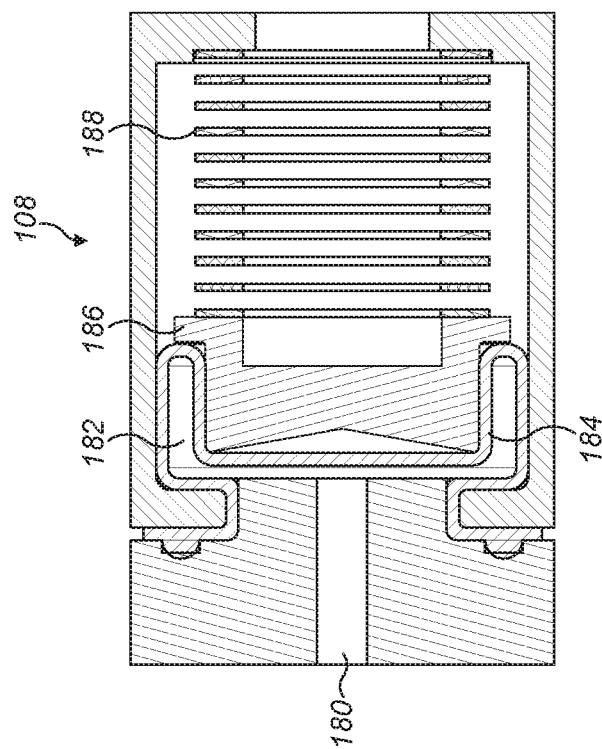

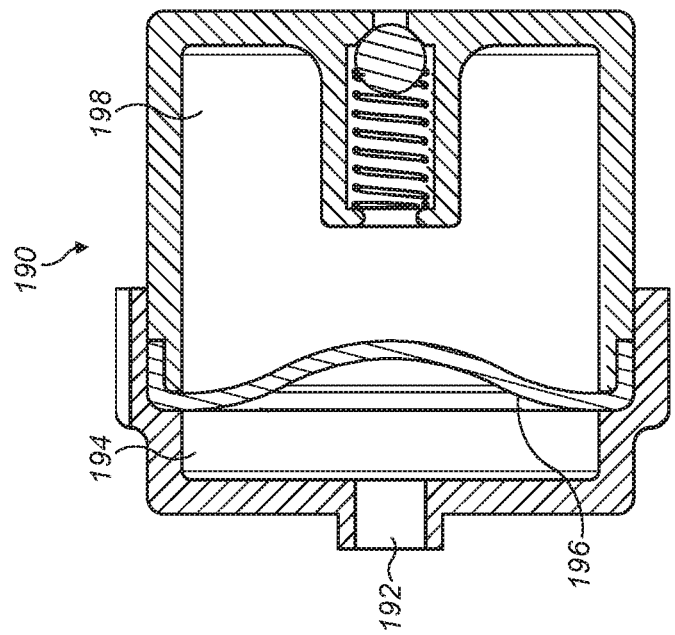
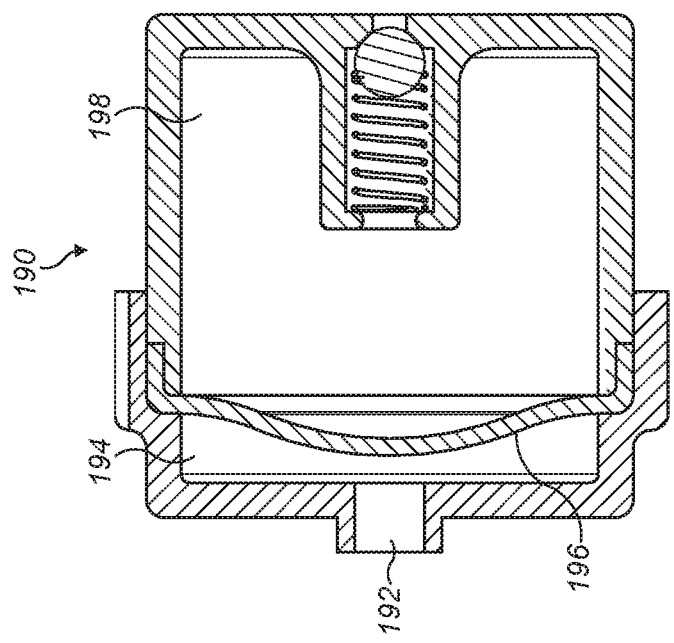

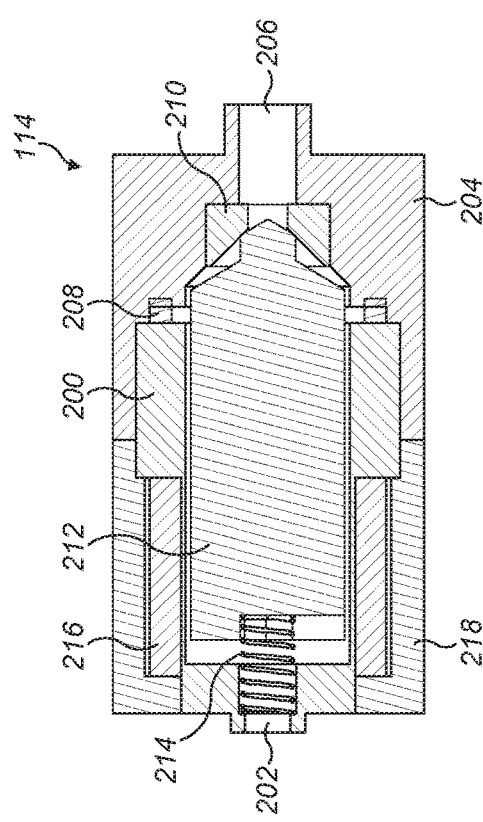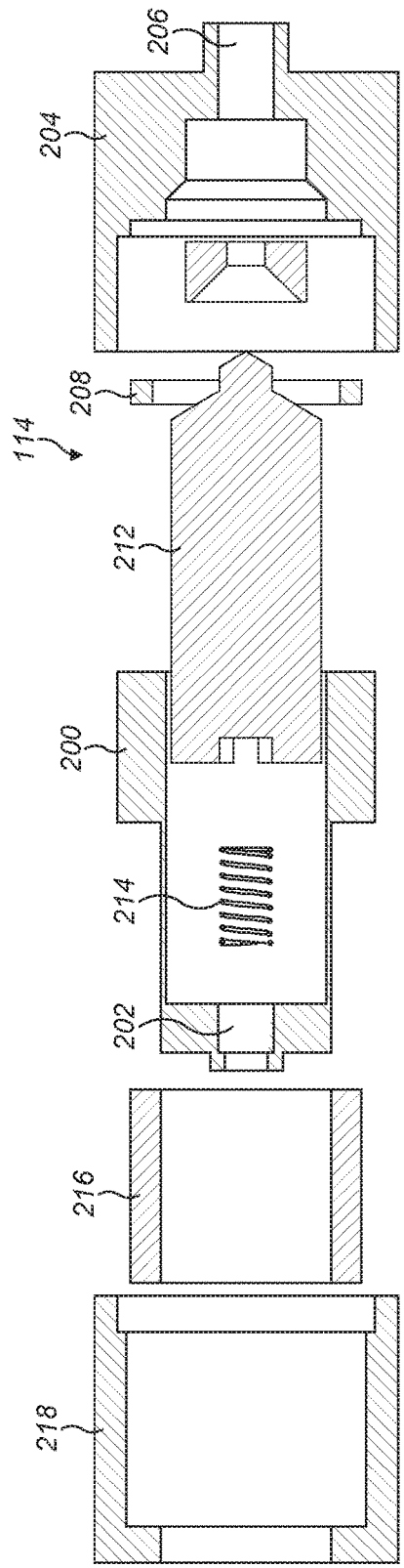
FIG. 16(a)
FIG. 16(b)

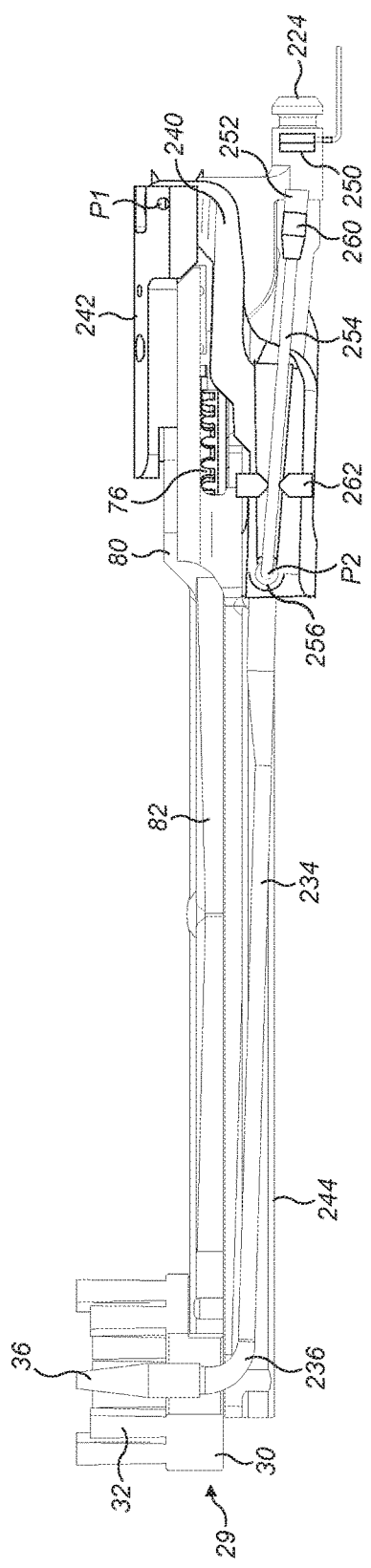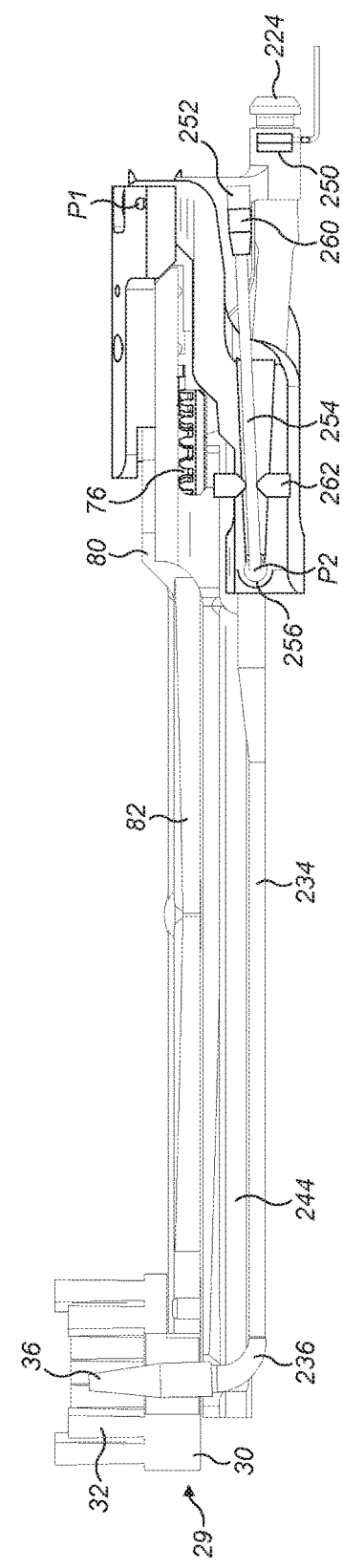
FIG. 19(a)
FIG. 19(b)

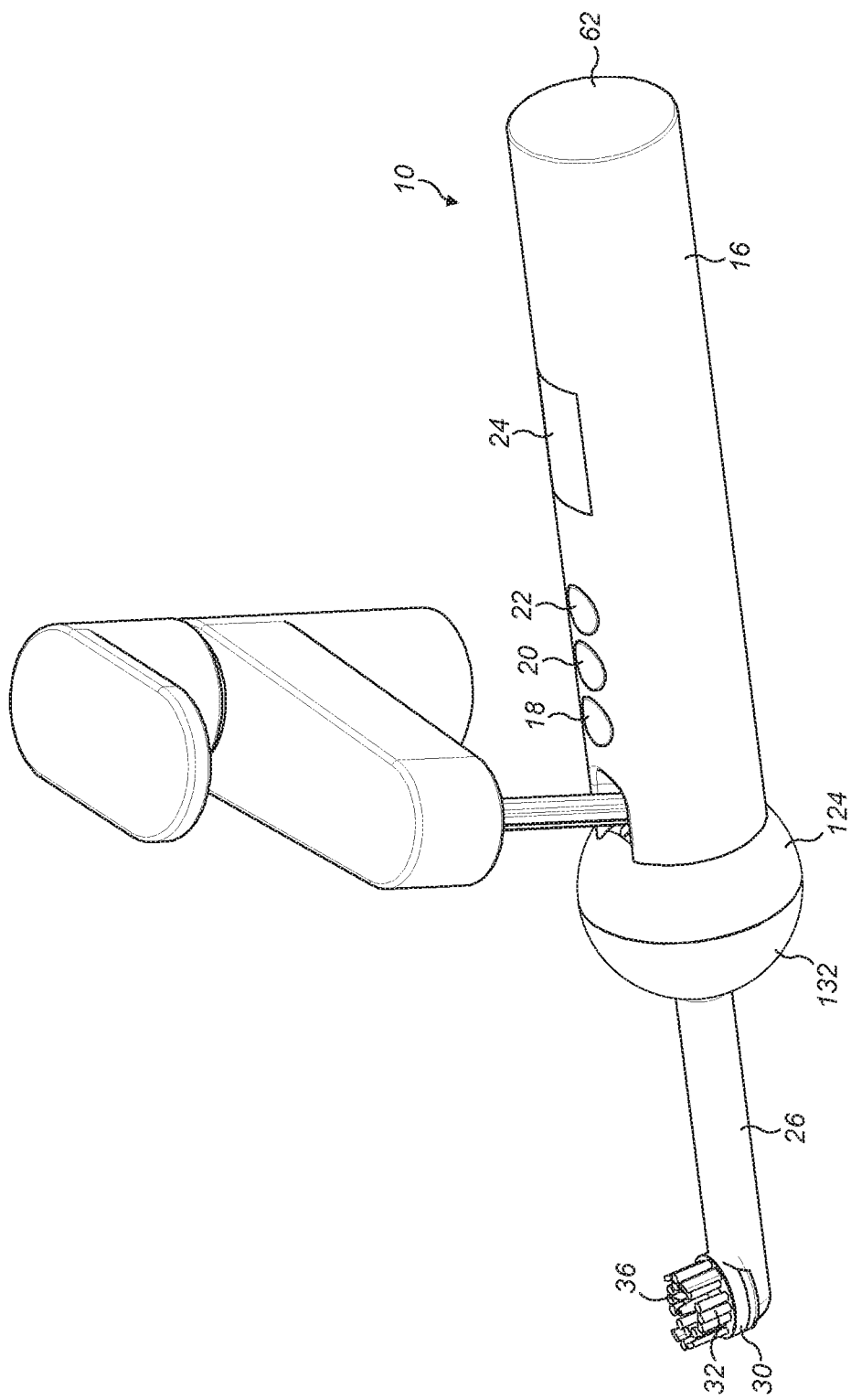

CLEANING APPLIANCE

REFERENCE TO RELATED APPLICATIONS

This application claims the priority of United Kingdom Application No. 1508366.0, filed May 15, 2015, the entire contents of which is incorporated herein by reference.

FIELD OF THE INVENTION

The present invention relates to a cleaning appliance. The cleaning appliance is preferably a handheld cleaning appliance, and is preferably a surface treating appliance. In preferred embodiments of the invention, the appliance is a dental cleaning appliance. In a preferred embodiment, the appliance is an electric toothbrush having a fluid delivery system for delivering a fluid to the teeth of the user. This fluid may be toothpaste, or a fluid for improved interproximal cleaning. Alternatively, the appliance may not include any bristles or other elements for brushing teeth, and may be in the form of a dedicated interproximal cleaning appliance. The invention also relates to a cleaning tool for use with a dental cleaning appliance, and to a handle for use with a dental cleaning appliance.

BACKGROUND OF THE INVENTION

Electric toothbrushes generally comprise a cleaning tool which is connected to a handle. The cleaning tool comprises a stem and a brush head bearing bristles for brushing teeth. The brush head comprises a static section which is connected to the stem, and at least one moveable section which is moveable relative to the static section, for example with one of a reciprocating, oscillating, vibrating, pivoting or rotating motion, to impart a brushing movement to bristles mounted thereon. The stem houses a drive shaft which couples with a transmission unit within the handle. The transmission unit is in turn connected to a motor, which is driven by a battery housed within the handle. The drive shaft and the transmission unit convert rotary or vibratory motion of the motor into the desired movement of the moveable section of the brush head relative to the static section of the brush head.

It is known to incorporate into an electric toothbrush an assembly for generating a jet of fluid for interproximal cleaning. For example, U.S. Pat. No. 8,522,384 describes an electric toothbrush in which the handle of the toothbrush defines a fluid chamber for storing a liquid such as water, and a slidable cover for enabling the fluid chamber to be accessed for replenishment by a user. A fluid path connects the fluid chamber to a nozzle located on a static portion of the brush head. A pump located within the fluid path is actuated upon user operation of an actuator on the handle to pump fluid from the fluid chamber to the nozzle for release under pressure from the nozzle.

SUMMARY OF THE INVENTION

In a first aspect, the present invention provides a dental cleaning appliance comprising a handle, a fluid delivery system for delivering a burst of working fluid to the teeth of a user, at least part of the fluid delivery system being moveable relative to the handle as the appliance is moved along the teeth of the user, a sensor for providing an output which varies with movement of said at least part of the fluid delivery system relative to the handle, and a control circuit for actuating the delivery of working fluid to the teeth of the user depending on the output from the sensor.

A part of the fluid delivery system which is moveable relative to the handle preferably comprises a nozzle from which the burst of working fluid is delivered to the teeth of a user. The nozzle preferably extends along a nozzle axis, which passes through a fluid outlet located at the tip of the nozzle. The nozzle axis may be aligned generally orthogonal to the longitudinal axis of the handle.

The nozzle is preferably formed from resilient material, such as an elastomeric material or a rubber.

The nozzle may be moveable relative to the handle in such a manner that the fluid outlet can move relative to the nozzle axis. For example, the nozzle may be configured to bend. For example, as the nozzle is moved along the teeth of a user during use of the appliance, the tip of the nozzle may deflect relative to the base of the nozzle, and especially when the nozzle engages a side of a tooth after having entered an interproximal gap. This deflection of the nozzle relative to the handle may cause the output from the sensor to vary, in response to which the control circuit may actuate the delivery of a burst of working fluid to the teeth of the user to dislodge matter located within the gap.

Alternatively, the nozzle may be moveable relative to the handle in a direction which extends generally parallel to or generally along the nozzle axis. The nozzle is preferably biased for movement relative to the handle in such a direction that the nozzle is urged against a user's teeth during use of the appliance. As the nozzle enters an interproximal gap as the nozzle is moved along the user's teeth, this movement of the nozzle relative to the handle causes the output from the sensor to vary, in response to which the control circuit actuates the delivery of a burst of working fluid to the teeth of the user to dislodge matter located within the gap.

The sensor may be arranged to detect directly the movement of the nozzle relative to the handle. For example, the sensor may be located adjacent to the nozzle. Alternatively, the sensor may be arranged to detect movement of a component which is connected to, and moveable with, the nozzle. For example, an arm may be connected to the nozzle, and the sensor may be arranged to detect movement of the arm relative to the handle.

A part of the fluid delivery system which is moveable relative to the handle preferably comprises a fluid conduit for conveying the burst of working fluid to the nozzle. The nozzle is preferably moveable with the fluid conduit. For example, the fluid conduit may be connected directly to the nozzle. As an alternative, the end of the fluid conduit may engage or abut the base of the nozzle so that the nozzle is pushed along the nozzle axis in response to movement of the fluid conduit relative to the handle.

The nozzle is preferably biased for movement relative to the handle in a direction which urges the nozzle against a user's teeth during use of the appliance. As mentioned above, the nozzle may be connected to an arm, and that arm may be biased for movement relative to the handle in a direction which urges the nozzle against a user's teeth during use of the appliance. For example, the arm may be urged to move in that direction by a resilient member which engages the arm. Alternatively, the arm may be deformed elastically in such a manner that relaxation of the arm urges the nozzle against the user's teeth. In this case, the fluid conduit moves with the nozzle as it is urged towards the user's teeth.

In a preferred embodiment, the fluid conduit is biased for movement relative to the handle in a direction which urges the nozzle against a user's teeth during use of the appliance.

This fluid conduit may thus server to bias the nozzle for movement relative to the handle in such a direction that the nozzle is urged against a user's teeth during use of the appliance. As discussed above, the nozzle may be connected to the end of the fluid conduit so that it moves with the fluid conduit relative to the handle. Alternatively, the nozzle may be secured to a body of the appliance by resilient means, for example a resilient annular flange extending outwardly from the nozzle, which urges the nozzle against the end of the fluid conduit so that it moves with the fluid conduit as the fluid conduit moves relative to the handle. This flange may also provide a seal between the nozzle and the body which inhibits the ingress of ejected working fluid or other material into the body of the appliance from around the nozzle.

The fluid conduit may be moveable relative to the handle in one of a number of different ways. For example, the fluid conduit may be slidable, rotatable or otherwise translatable relative to the handle. Alternatively, the fluid conduit may be extendable or expandable.

In a second aspect, the present invention provides a dental cleaning appliance comprising a handle, and a fluid delivery system comprising a nozzle for delivering a burst of working fluid to the teeth of a user, and a fluid conduit for conveying working fluid to the nozzle, the fluid conduit being moveable relative to the handle, the nozzle being moveable with the fluid conduit, the fluid conduit being biased for movement in a direction which urges the nozzle against a user's teeth during use of the appliance.

In a preferred example, the fluid conduit is moveable relative to the handle about an axis. The fluid conduit is preferably pivotable about the axis. This axis is preferably substantially orthogonal to the longitudinal axis of the handle. The axis is preferably angled to the nozzle axis, and is more preferably substantially orthogonal to the nozzle axis.

The fluid conduit preferably has a rigidity which is such that the fluid conduit does not deform, bend or kink as the fluid conduit moves relative to the handle or as the nozzle is urged against the teeth of the user during use of the appliance. The fluid conduit is preferably formed from one of metallic and plastics material. However, if an arm is used to bias the nozzle towards the user's teeth, the fluid conduit may be formed from a more flexible material to allow the fluid conduit to move freely relative to the handle.

The fluid conduit is preferably biased for movement relative to the handle by a resilient member. The resilient member may engage a component to which the fluid conduit is connected. For example, the nozzle may be connected to an arm, and that arm may be biased for movement relative to the handle. As the arm moves relative to the handle, the fluid conduit may move relative to the handle, preferably about an axis. Alternatively, the resilient member may engage the fluid conduit. The resilient member preferably exerts a force on the fluid conduit, or the arm, which is of a sufficient magnitude to allow the nozzle to move, against the biasing force of the resilient member, as it is pressed against the user's teeth, and without exerting an excessive force on the teeth which is uncomfortable for the user.

The resilient member may be located between the body and the fluid conduit, so as to urge the fluid conduit to move about the axis in a direction which urges the nozzle against a user's teeth during use of the appliance. The resilient member may be in the form of a spring or another elastic element. The resilient member may engage the fluid conduit directly, or it may engage a component of the appliance which is connected to the fluid conduit and moveable therewith. Such a component may be a support for supporting the fluid conduit for movement relative to the handle, or an arm connected to the fluid conduit.

In a preferred embodiment, the resilient member forms a part of the fluid delivery system, and is preferably in the form of a resilient fluid conduit which is connected to the pivotable, or moveable, fluid conduit. That resilient fluid conduit may be twisted, bent, compressed or otherwise deformed so as to exert a force on the pivotable fluid conduit which urges it to move relative to the handle in a direction which urges the nozzle against a user's teeth during use of the appliance.

Thus, the fluid delivery system may comprise a nozzle from which the burst of working fluid is delivered to the teeth of a user, a relatively rigid fluid conduit which is pivotable about an axis, and a relatively flexible, resilient fluid conduit for urging the pivotable fluid conduit to pivot about the axis in a direction which urges the nozzle against a user's teeth during use of the appliance.

The pivotable fluid conduit is preferably located between the nozzle and the resilient fluid conduit. For example the resilient fluid conduit may be connected to one end of the pivotable fluid conduit, with the nozzle being connected to, or otherwise engaging, the other end of the pivotable fluid conduit.

The pivotable fluid conduit preferably has a plurality of sections. For example, the fluid conduit may have a first section and a second section which extends in a different direction to the first section. In other words, the fluid conduit is preferably non-linear. The resilient fluid conduit is preferably connected to the first section. The second section may be angled to the first section, and may be substantially orthogonal to the first section. Alternatively, the second section may be curved. The nozzle is preferably connected to, or otherwise engages, the second section, and so at least part of the second section is preferably substantially collinear with the nozzle. Where the second section is curved, at least an end portion of the second section, which engages the nozzle, may be collinear with the nozzle. The first section is preferably straight, and is preferably longer than the second section, and so the pivotable fluid conduit may be generally L-shaped.

The sensor is preferably arranged to provide an output which varies with movement of a moveable part of the fluid delivery system relative to the handle, and so, in this embodiment, with movement of one of the nozzle, the pivotable fluid conduit, and the resilient fluid conduit. The sensor may be in the form of a motion detector.

The sensor may be arranged to detect motion of a moveable part of the fluid delivery system directly. For example, the sensor may be in the form of a light detector, such a camera or a light sensor, for receiving light reflected from the moveable part of the fluid delivery system. Alternatively, the moveable part of the fluid delivery system may be formed from magnetic material, with the sensor being arranged to detect the movement of that magnetic part of the fluid delivery system from the variation in the magnetic field experienced by the sensor. For example, the sensor may be a Hall effect sensor.

Alternatively, the sensor may be arranged to detect motion of a component which is moveable with the moveable part of the fluid delivery system. That component may comprise a light reflective component or light emitting component. Alternatively, the component may comprise a deformable member which is connected to the moveable part of the fluid delivery system, and the sensor may be arranged to detect the deformation of that deformable member. For example, the deformable member may be in the form of an elastic rod which is connected to the moveable part of the fluid delivery system, and the sensor may be in the form of a strain gauge for outputting a signal which varies with the strain on the deformable member.

Preferably, the component comprises a magnet, and the sensor is preferably arranged to detect the movement of the magnet from the variation in the magnetic field experienced by the sensor as the magnet moves relative to the sensor. The magnet may be connected directly to the moveable part of the fluid delivery system. Alternatively, to facilitate assembly the magnet may be connected to a component which is itself connected to, or carried by, a moveable part of the fluid delivery system. For example, the appliance may comprise a support for supporting a moveable part of the fluid delivery system for movement relative to the handle. The support is preferably moveable relative to the handle with the moveable part of the fluid delivery system. In a preferred embodiment, the support is connected to the pivotable fluid conduit.

The magnet may be connected directly to the support. However in a preferred embodiment the appliance comprises an arm which connected to the support for movement therewith, with the magnet being connected to, or defining, part of the arm. The magnet is preferably connected to a free end of the arm.

The arm is preferably moveable relative to the support. The arm preferably has a first end which is connected to the support for movement therewith, and a second end which is remote from the first end. A magnet, or magnetic material, is preferably located at the second end of the arm. The arm is preferably pivotably moveable relative to the support about a second pivot axis. The second pivot axis may be located at the first end of the arm, or it may be located between the ends of the arms, with the distance between the second pivot axis and the second end of the arm being greater than the distance between the second pivot axis and the first end of the arm. As a result, for a given rotation of the arm about the second pivot axis, which rotation results from the pivoting movement of the support relative to the handle, the extent of the movement of the second end of the arm about the second pivot axis is greater than the extent of the movement of the support relative to the handle.

This can enable relatively small movements of the moveable part of the fluid delivery system relative to the handle to be converted into relatively large movements of the second end of the arm relative to the handle. This can facilitate the detection of the movement of the moveable part of the fluid delivery system relative to the handle, and can enable the sensor to be located at a convenient location within the appliance for detecting the movement of the second end of the arm. For example, the sensor may be located in the handle of the appliance to facilitate its connection to the control circuit, which is also preferably located in the handle of the appliance. A battery for supplying power to the control circuit is also preferably located in the handle of the appliance. The battery is preferably a rechargeable battery.

The appliance preferably comprises a head, and a stem extending between the head and the handle. The nozzle preferably protrudes outwardly from the head. The resilient fluid conduit is preferably located in the stem. The pivotable fluid conduit thus extends between the stem and the head. In a preferred embodiment, the first section of the pivotable fluid conduit is located in the stem, and the second portion of the pivotable fluid conduit is located in the head.

The nozzle is preferably moveable relative to the head. The nozzle is preferably biased for movement relative to the head in a direction which extends away from the head.

The nozzle is preferably moveable between a distal position and a proximal position relative to the head. The nozzle is preferably biased for movement towards the distal position. The control circuit is preferably configured to actuate the delivery of working fluid to the teeth of the user in response to movement of the nozzle to, or from, the distal position.

The control circuit may be configured to actuate the delivery of working fluid to the teeth of the user depending on the magnitude of the output from the sensor. Preferably, the control circuit is configured to actuate the delivery of working fluid to the teeth of the user depending on the rate of change of the output from the sensor. The output from the sensor is preferably in the form of a voltage.

In a preferred embodiment, the control circuit is configured to sample the output from the sensor at predetermined intervals to provide a series of sampled sensor outputs, S. For example, the predetermined interval may be in the range from 5 to 25 ms, and in a preferred embodiment is 10 ms. The rate of change, Sr, of the sampled sensor outputs S is calculated from the difference between consecutive sampled sensor outputs S. In the preferred embodiment, Sr is calculated every 10 ms.

The control circuit is further configured to determine an average rate of change of the sensor output, Sa, by calculating the average value of the n most recent values of Sr. The integer n is preferably in the range from 5 to 40, and in the preferred embodiment is 10. A value for Sa is thus also calculated every 10 ms. From the value of Sa, it can be determined whether, over a time period of 100 ms, the nozzle is tending to move towards the distal position, move away from the distal position, or remain in a relatively stationary position relative to the handle, for example, at the distal position.

The control circuit is preferably configured to actuate the delivery of working fluid to the teeth of the user depending on the value of Sa. The control circuit may be configured to actuate the delivery of working fluid to the teeth of the user depending on the variation with time of the value of Sa. For example, the control circuit may be configured to actuate the delivery of working fluid to the teeth of the user when (i) the value of Sa has risen above, or fallen below, a first pre-set threshold value—which is indicative of the nozzle moving towards its distal position—and (ii) the value of Sa has subsequently fallen below, or risen above, a second pre-set threshold value—which is indicative of the nozzle being located within an interproximal gap, or moving away from an interproximal gap towards its proximal position.

An advantage associated with the actuation of the delivery of working fluid to the teeth of the user in response to movement of the nozzle away from the distal position is that the working fluid is not ejected from the nozzle when the implement is moved away from the teeth of the user, for example at the end of a cleaning operation.

As mentioned above, the pivotable fluid conduit is preferably moveable about a pivot axis. As the nozzle moves between its distal and proximal positions relative to the head, the nozzle thus preferably moves along a curved path, preferably in the shape of an arc which has a centre which is located on the pivot axis of the fluid conduit. The extent of the angular movement of the tip of the nozzle about the pivot axis is preferably in the range from 1 to 5°. In a preferred embodiment, the tip of the nozzle moves about the pivot axis by an angle of approximately 2.5° as the nozzle moves from the distal position to the proximal position. Thus, the nozzle may be considered to be biased for movement in a plane containing the nozzle axis, and along a curved or circular path located within that plane. When the nozzle is in its distal position, the nozzle axis is preferably aligned at an angle of 90° to the longitudinal axis of the handle.

To facilitate the movement of the nozzle along the teeth of user during use of the appliance, the head preferably comprises engagements for engaging the teeth of the user, with the nozzle being moveable relative to the engagements as it moves between its distal and proximal positions. For user comfort, the engagements may be formed from resilient or elastomeric material. The engagements may have a substantially flat upper surface, a curved upper surface, or a stepped upper surface. For example, the engagements may have a concave upper surface. When the nozzle is in its distal position relative to the head, the tip of the nozzle preferably protrudes outwardly beyond at least some of the engagements so that, when the nozzle is pressed against a user's teeth, the nozzle moves away from the distal position and towards the proximal position.

The appliance may be in the form of a dedicated interproximal cleaning appliance for cleaning between the gaps in the user's teeth. As the nozzle is moved along the teeth of the user, the entry of the nozzle into a gap between adjacent teeth is detected through the variation in the output from the sensor resulting from the movement of the magnet relative to the sensor. For such an appliance, the engagements may comprise a single resilient member which surrounds the nozzle. Alternatively, the engagements may comprise a plurality of resilient members arranged adjacent to the nozzle. The resilient members may be located on opposite sides or ends of the head, or arranged about the nozzle. For example, the resilient members may be arranged circumferentially about the nozzle. The resilient member(s) may be formed from elastomeric material.

Alternatively, the appliance may be in the form of a toothbrush which has the additional function of improved interproximal cleaning through the emission of a burst of working fluid into the interproximal gap. Where the appliance is in the form of a toothbrush, the engagements preferably comprises a plurality of bristles. The bristles are preferably arranged around the nozzle, and may be arranged circumferentially about the nozzle.

The plurality of bristles may be attached to a static section of the head, which section is not moveable relative to the handle. Alternatively, or additionally, a plurality of bristles may be attached to a moveable section of the head, which section is moveable relative to the handle. In a preferred embodiment, the appliance comprises a brush unit comprising a bristle carrier and a plurality of bristles mounted on the bristle carrier, with the bristle carrier being moveable relative to the handle. The nozzle is preferably biased for movement relative to the brush unit in a direction extending away from the brush unit.

In addition to the movement of the nozzle relative to the brush unit, the brush unit is preferably moveable relative to the nozzle. The movement of the brush unit relative to the nozzle, to enable the ends of the bristles to be swept over the surfaces of the teeth of the user, may thus be independent from the movement of the nozzle relative to the handle to cause a burst of working fluid to be delivered to the teeth of the user. This can prevent any spurious or otherwise undesired actuation of the delivery of working fluid to the teeth of the user resulting from movement of the bristles relative to the handle.

The bristle carrier may translate, rotate, pivot or vibrate relative to the nozzle. In a preferred embodiment, the bristle carrier is arranged to orbit about the nozzle, and preferably about the axis of the nozzle when the nozzle is in its distal position. The brush unit preferably extends at least partially about the nozzle. For example, the bristle carrier may be curved or partially annular, for example C-shaped, so as to extend partially about the nozzle. Alternatively, the bristle carrier may be annular in shape, or otherwise shaped to surround the nozzle. For example, the bristle carrier may comprise an aperture through which the nozzle protrudes.

In a third aspect, the present invention provides a dental cleaning appliance comprising a handle, a fluid delivery system for delivering a burst of working fluid to the teeth of a user, the fluid delivery system comprising a nozzle from which the burst of working fluid is delivered to the teeth of the user, a brush unit comprising a bristle carrier and a plurality of bristles mounted on the bristle carrier, the brush unit extending at least partially about the nozzle, and a drive unit for driving movement of the bristle carrier relative to the nozzle.

The appliance preferably includes a drive unit for driving the movement of the bristle carrier, and a transmission unit for converting a rotary motion generated by the drive unit into an orbital motion of the bristle carrier. The drive unit is preferably located in the handle of the appliance. The drive unit preferably comprises a motor, which is powered by the battery, and a first set of gears.

The transmission unit preferably comprises a second set of gears, a crank, and a connecting rod which connects the bristle carrier to the crank. The connecting rod is preferably located within the stem. The pivotable, or moveable, fluid conduit is also preferably located within the stem, and so this fluid conduit is preferably located alongside the connecting rod.

The fluid delivery system may comprise a source of pressurized working fluid and a valve. The source of pressurized working fluid and the valve are preferably located in the handle of the appliance. The control circuit is preferably configured to open the valve for a period of time depending on the output from the sensor. The valve is preferably opened for a time period which is sufficient to allow a burst of pressurized working fluid having a selected volume to pass from the source to the nozzle for delivery to the teeth of the user. This time period is preferably less than 1 second, more preferably less than 0.5 seconds, and even more preferably less than 0.25 seconds.

The valve is preferably a solenoid valve.

The working fluid is preferably a liquid working fluid, and is preferably water. Where the working fluid is a liquid working fluid, the source of pressurized working fluid is preferably in the form of a hydraulic accumulator. The hydraulic accumulator is preferably one of a spring-type accumulator, and a gas-charged accumulator. The accumulator preferably comprises a fluid chamber for storing working fluid under pressure. The accumulator is preferably arranged to store working fluid at a pressure in the range from 4 to 7 bar. The fluid chamber preferably has a capacity in the range from 0.1 to 1 ml.

The use of a combination of a hydraulic accumulator and a solenoid valve can allow bursts of working fluid of substantially uniform pressure and duration to be delivered to the teeth of a user.

The fluid delivery system preferably comprises a pump for supplying working fluid to the accumulator when the solenoid valve is in a closed position. The pump is arranged to draw working fluid through a fluid inlet. The pump is preferably in the form of a diaphragm pump. Alternatively, the pump may be a piston pump. A first one-way valve is preferably located between the fluid inlet and the pump to prevent working fluid from returning to the fluid inlet. A second one-way valve is preferably located between the pump and the accumulator to prevent working fluid from returning to the pump from the accumulator.

In a fourth aspect, the present invention provides a dental cleaning appliance comprising a fluid delivery system comprising a fluid inlet, a pump for drawing a working fluid through the fluid inlet, a hydraulic accumulator for receiving working fluid from the pump, a nozzle having a fluid outlet, and a valve located between the accumulator and the nozzle, the valve having an open position for enabling the accumulator to deliver a burst of working fluid to the nozzle and a closed position for enabling the accumulator to be replenished under the action of the pump; and a control circuit for actuating the pump and for controlling the position of the valve.

The capacity of the fluid chamber of the accumulator may be substantially the same as the volume of a single burst of working fluid. For example, the fluid chamber may have a capacity of around 0.25 ml, and a single burst of working fluid may have a volume of around 0.25 ml. In this case, the accumulator is substantially emptied following the delivery of a single burst of working fluid to the nozzle, and so requires replenishment before another burst of working fluid can be delivered. The time taken to replenish the accumulator is preferably in the range from 0.25 to 1 second, during which time the control circuit is preferably arranged to inhibit the delivery of working fluid to the nozzle, irrespective of the output from the sensor.

Alternatively, the capacity of the fluid chamber of the accumulator may be larger than the volume of a single burst of working fluid. For example, the fluid chamber may have a capacity of around 0.75 ml, and a single burst of working fluid may have a volume of around 0.25 ml. In this case, the solenoid valve is held in an open position by the control circuit for a time required for a selected volume of working fluid to be ejected from the accumulator. For example, the solenoid valve may be held in an open position for a time period in the range from 1 to 100 ms, more preferably in the range from 5 to 50 ms, and in a preferred embodiment for a time period of 30 ms, to allow a single burst of working fluid having a volume of 0.25 ml to be delivered to the nozzle.

In this case, the accumulator is substantially emptied following the delivery of three bursts of working fluid to the nozzle, although the time required to replenish the accumulator following the delivery of those bursts of working fluid to the nozzle will increase, for example to a time period in the range from 0.75 to 3 seconds, in view of the larger capacity of the accumulator. As opposed to increasing the capacity of the fluid chamber of the accumulator, the volume of a single burst of working fluid may be decreased. For example, the fluid chamber may have a capacity of around 0.25 ml, and a single burst of working fluid may have a volume of around 0.08 ml. In this case, the solenoid valve is held in an open position by the control circuit for a time required for a selected volume of working fluid to be ejected from the accumulator, for example for a time period of around 10 ms, to allow a single burst of working fluid having a volume of 0.08 ml to be delivered to the nozzle. In this latter case, again the accumulator is substantially emptied following the delivery of three bursts of working fluid to the nozzle, but the time required to replenish the accumulator following the delivery of those bursts of working fluid to the nozzle will remain in the range from 0.25 to 1 second.

As discussed above, the control circuit may be arranged to deliver a single burst of working fluid depending on the output from the sensor. However, the control circuit may be arranged to deliver a series of bursts of working fluid depending on the output from the sensor. Within a series, the time period between successive bursts of working fluid is preferably substantially equal, preferably in the range from 1 to 25 ms, and more preferably in the range from 2 to 10 ms, so that the entire series of bursts may be delivered to a single interproximal gap. This can allow for a slight variation in the position of the tip of the nozzle relative to interproximal gap between each successive burst, and so potentially improving the removal of material from within the interproximal gap.

In a fifth aspect, the present invention provides a dental cleaning appliance comprising a handle; a fluid delivery system for delivering working fluid to the teeth of a user; and a control circuit for actuating the delivery of working fluid to the teeth of the user depending on a received input, wherein, for each input, the control circuit is arranged to actuate the delivery of a series of bursts of working fluid to the teeth of the user. The input may be generated by a sensor. Alternatively, the input may be generated in response to a user action on the appliance, for example, the operation of a button of the appliance.

The number of bursts within a series is preferably in the range from two to ten. The volume of working fluid delivered to the teeth of a user in a series of bursts is preferably in the range from 0.1 to 1 ml. Within a series of bursts, each burst of working fluid preferably has substantially the same, which is preferably in the range from 0.05 to 0.5 ml, and more preferably in the range from 0.05 to 0.25 ml.

The capacity of the fluid chamber of the accumulator may be substantially the same as the volume of working fluid which is ejected from the appliance in a single series of bursts of working fluid. For example, the fluid chamber may have a capacity of around 0.25 ml, and a single series of bursts of working fluid may eject a volume of working fluid of around 0.25 ml. In this case, the fluid chamber requires replenishment before another series of bursts of working fluid can be delivered. Alternatively, the capacity of the fluid chamber of the accumulator may be greater than the volume of working fluid which is ejected from the appliance in a single series of bursts of working fluid. For example, the fluid chamber may have a capacity of around 0.75 ml, and a single series of bursts of working fluid may have a volume of around 0.25 ml. In this case, the fluid chamber requires replenishment following the delivery of three series of bursts of working fluid.

The appliance preferably comprises a fluid reservoir for storing working fluid, preferably a liquid working fluid, and from which working fluid is supplied to the fluid delivery system. The fluid reservoir preferably has a capacity in the range from 5 to 50 ml. For example, a fluid reservoir having a capacity of 25 ml, used in combination with an accumulator having a fluid capacity of 0.25 ml, can supply a sufficient quantity of working fluid to the accumulator to allow up to 100 bursts, or 100 series of bursts, of 0.25 ml of working fluid to be delivered to the teeth of a user.

The fluid reservoir is preferably refillable. The fluid reservoir thus preferably comprises a fluid port through which the fluid reservoir may be replenished with working fluid by the user. The fluid port may be located in a wall which delimits the fluid reservoir, or it may be located remotely from the fluid reservoir and placed in fluid communication with the fluid reservoir by a fluid conduit which extends from the fluid port to the fluid reservoir.

The control circuit may be configured to generate an alert to advise the user that the fluid reservoir requires replenishment. For example, the accumulator may comprise a sensor for providing a signal to the control circuit which is indicative of the volume of working fluid stored within the accumulator. The sensor may comprise a pressure sensor for providing a signal which is indicative of the pressure of working fluid stored within the accumulator. For example, the sensor may output a signal to the control circuit when the pressure within the accumulator has exceeded a pre-set threshold value. Alternatively, the sensor may be in the form of a sensor which contacts a part of the accumulator, such as a piston or a diaphragm, which moves as the accumulator fills with working fluid. For example, that sensor may output a signal to the control circuit when the diaphragm has contacted the sensor. During replenishment of the accumulator following the delivery of working fluid to the nozzle, the control circuit may be configured to de-activate the pump upon receipt of such a signal. If such a signal is not received within a predetermined time period, for example, in the range from 0.5 to 2 seconds, following actuation of the pump, this can be indicative of there being insufficient working fluid stored within the fluid reservoir to enable the accumulator to be fully replenished. In this case, the control circuit is preferably configured to, following the expiration of that time period, generate an alert to advise the user that the fluid reservoir requires replenishment. That alert may be in the form of a visual alert generated on a display of the appliance, or an audible alert.

The handle of the appliance may comprise the fluid reservoir. For example, the fluid reservoir may be fully contained within the body of the handle. Alternatively, an external wall of the handle may at least partially delimit the fluid reservoir. At least part of that external wall may be transparent to allow a user to see the volume of working fluid contained within the fluid reservoir. To replenish such a fluid reservoir, the fluid port may be exposed manually by the user through moving a cover on the body of the handle, or through removing a bung or other closure device from the fluid port.

The fluid reservoir may be housed within the stem. As above, an external wall of the stem may at least partially delimit the fluid reservoir, and at least part of that external wall may be transparent to allow a user to see the volume of working fluid contained within the fluid reservoir.

As an alternative to housing the fluid reservoir within the stem, the fluid reservoir may be connected to the stem so as to be located externally of the stem. This can allow the fluid reservoir to be detached from the stem for replenishment or replacement as required. Alternatively, the fluid reservoir may be partially delimited by an external wall which is connected to the stem. Again, at least part of that external wall may be transparent to allow a user to see the volume of working fluid contained within the fluid reservoir.

To maximize the capacity of the fluid reservoir and to provide for a relatively even weight distribution about the longitudinal axis of the appliance, the fluid reservoir preferably extends about, or surrounds, the stem.

The appliance preferably comprises a cleaning tool connected to the handle. The cleaning tool comprises the nozzle of the fluid delivery system. The cleaning tool preferably comprises the head and the stem of the appliance.

The cleaning tool is preferably detachably connected to the handle. This can allow the cleaning tool to be replaced, for example when a non-refillable fluid reservoir has become depleted, or when the bristles and/or the nozzle of the appliance have become worn. This can also allow a different cleaning tool to be connected to the handle, for example for use by a different user.

In a sixth aspect, the present invention provides a dental cleaning appliance comprising a handle, and a cleaning tool detachably connected to the handle, the cleaning tool comprising a nozzle for delivering a burst of working fluid to the teeth of a user, a stem extending between the handle and the nozzle, and a fluid reservoir for storing working fluid, the fluid reservoir being connected to and extending around the stem.

The fluid reservoir preferably comprises an external wall which surrounds part of the stem. That part of the stem is preferably located adjacent to the handle of the appliance. At least part of that external wall is preferably transparent, and is preferably formed from transparent plastics material to allow a user to see the volume of working fluid within the fluid reservoir. In a preferred embodiment, the external wall is a single molded component formed from transparent material.

The external wall of the fluid reservoir preferably has one of a curved shape, a convex shape, and a faceted shape. The external wall may have a curvature which is one of ellipsoidal, spheroidal and spherical.

As mentioned above, the appliance may comprise a fluid port through which the fluid reservoir is replenished with working fluid. The fluid port may be permanently exposed, with a bung or other closure device being removably located within the fluid port to inhibit leakage of working fluid from the fluid reservoir through the fluid port. Preferably, the fluid port is located on an external collar, which is moveable relative to the handle between a first position in which the fluid port is exposed to allow the fluid reservoir to be replenished, and a second position in which the fluid port is occluded. This can enable the fluid port to be easily and rapidly exposed by the user to replenish the fluid reservoir.

In a seventh aspect, the present invention provides a dental cleaning appliance comprising a handle, a fluid reservoir for storing a working fluid, a fluid delivery system for receiving working fluid from the fluid reservoir, and for delivering a burst of working fluid to the teeth of a user, and an external collar comprising a fluid port, the collar being moveable relative to the handle between a first position in which the fluid port is exposed to allow the fluid reservoir to be replenished, and a second position in which the fluid port is occluded.

When the collar is in the second position, the fluid port may be in a position in which it engages a seal which inhibits the leakage of working fluid through the fluid port. This seal may be located on an internal surface of a wall or other part of the handle which faces the fluid port when the collar is in the second position. Preferably, when the collar is in the second position, the fluid port is connected to the fluid delivery system so that working fluid may be supplied to the fluid delivery system through the fluid port rather than from an additional fluid port.

The collar may be slidable relative to the handle. Preferably, the collar is rotatable relative to the handle, and preferably about the longitudinal axis of the handle. The collar may be connected to the body of the handle for movement relative to the body of the handle. In a preferred embodiment, the collar is connected to the cleaning tool of the appliance, and is preferably located about the stem. The collar may rotate about the longitudinal axis of the stem. The collar may have one of a curved shape, a convex shape, and a faceted shape, and may have a curvature which is one of ellipsoidal, spheroidal and spherical.

The collar may be separate from the fluid reservoir. The fluid port may be connected to the fluid reservoir by a flexible conduit having an end which is connected to the fluid port and which moves with the collar as it is moved between the first position and the second position.

Alternatively, the collar may at least partially delimit the fluid reservoir, and may form part of the external wall of the reservoir. Thus, at least part of the external wall of the fluid reservoir may move relative to the handle as the collar portion of the external wall is moved between the first position and the second position. Seals may be placed between the moving part of the fluid reservoir and the other parts of the fluid reservoir, relative to which that part of the fluid reservoir moves, to inhibit the leakage of working fluid from between those parts of the fluid reservoir. However, in a preferred embodiment, the entire fluid reservoir, including the collar, external wall and any other component which delimits the fluid reservoir, is moveable relative to the handle.

For example, the fluid reservoir may comprise an inner wall which is connected to the external wall, and which moves with the external wall relative to the handle. The inner wall may be annular or tubular in shape, and located around the stem so as to provide a sleeve which surrounds the stem. The ends of the inner wall may be joined, for example using a welding technique or using an adhesive, to the external wall.

The entire inner wall, along with the external wall, may be formed from relatively rigid plastics material, so that the capacity of the fluid reservoir is fixed and is defined by the internal surfaces of the external wall and the inner wall. Alternatively, a part of the inner wall of the reservoir, or a separate component which partially delimits the fluid reservoir, may be moveable relative to the external wall to vary the volume of the fluid reservoir. This moveable member may be moved by a piston or other device which is actuated by the control circuit to reduce the volume of the fluid reservoir as working fluid is supplied to the fluid delivery system. This can inhibit the formation of an air lock within the fluid reservoir as working fluid is supplied to the fluid delivery system. The piston may be actuated by the control circuit simultaneously with the actuation of the pump to draw working fluid from the fluid reservoir so that the reduction in the volume of the fluid reservoir is equal to the volume of working fluid which is drawn from the fluid reservoir by the pump.

Alternatively, this moveable member may be moveable in response to a pressure difference established across the surfaces thereof as working fluid is supplied to the fluid delivery system. The appliance may comprise an expansion chamber located adjacent to the moveable member, preferably to one side of the moveable member, and which increases in volume as the volume of the fluid reservoir decreases as working fluid is supplied to the fluid delivery system.

In an eighth aspect, the present invention provides a dental cleaning appliance comprising a handle, a fluid reservoir for storing a working fluid, the fluid reservoir being at least partially delimited by a wall, preferably an external wall, and a movable member which is moveable relative to the wall to vary the volume of the fluid reservoir, a fluid delivery system for receiving working fluid from the fluid reservoir, and for delivering the working fluid to the teeth of a user, and an expansion chamber located adjacent to the moveable member and which increases in volume as the volume of the fluid reservoir decreases as working fluid is supplied to the fluid delivery system.

The expansion chamber may contain a pressurized gas which exerts a force on the moveable member which causes the moveable member to move as working fluid is supplied to the fluid delivery system. However, the expansion chamber is preferably open to the atmosphere to receive ambient air as the volume of the expansion chamber increases.

The external wall is preferably formed from relatively rigid material, and the moveable member is preferably formed from relatively flexible material. In a preferred embodiment, the moveable member comprises a diaphragm or bladder which is expandable in response to a pressure difference across the surfaces thereof.

The external wall preferably surrounds the diaphragm. The diaphragm is preferably annular or tubular in shape, and preferably has opposite ends which are connected to the external wall, preferably at diametrically opposed locations on the external wall. The wall and the diaphragm preferably extend about a common longitudinal axis so that as the diaphragm expands, the diaphragm expands outwardly away from the longitudinal axis.

The diaphragm preferably extends about the expansion chamber so that a relatively uniform force is applied over the surface of the diaphragm to pull the diaphragm towards the fluid reservoir as working fluid is supplied to the fluid delivery system. This can promote a uniform expansion of the diaphragm as working fluid is supplied to the fluid delivery system. To minimize the number of components of the appliance, preferably the diaphragm at least partially delimits the expansion chamber. For example, the diaphragm may be located between, and define a barrier between, the expansion chamber and the fluid reservoir. The expansion chamber is preferably annular in shape. The expansion chamber may be delimited by the diaphragm and the stem of the cleaning tool of the appliance. Alternatively, the expansion chamber may be delimited by the diaphragm and a wall which defines a port through which air enters the expansion chamber. The wall of the expansion chamber preferably extends around, and is coaxial with, the stem. The wall of the expansion chamber is preferably connected to the external wall and the diaphragm, and is preferably moveable with the external wall as it is moved relative to the stem. In other words, both the fluid reservoir and the expansion chamber are preferably moveable, or rotatable, relative to the stem.

As the diaphragm expands, the size and shape of the diaphragm approaches that of the external wall of the reservoir. In other words, when the diaphragm is in a fully expanded configuration, which occurs when the fluid reservoir is empty, the size and shape of the diaphragm are preferably substantially the same as the external wall of the reservoir. When the diaphragm is in a fully contracted or deflated configuration, which occurs when the fluid reservoir has been filled to capacity, the size and shape of the moveable member are preferably substantially the same as the wall of the expansion chamber. Thus, the expansion chamber preferably has a maximum volume which is substantially the same as the maximum volume of the fluid reservoir.

As mentioned above, the external wall of the fluid reservoir is preferably transparent, which allows the user to see both the contents of the fluid reservoir and, when the working fluid is water, the diaphragm. At least part of the diaphragm is preferably formed from colored material, or otherwise bears an identifier which serves to distinguish the cleaning tool of the appliance from others. This can allow a cleaning tool to bear an identifier which can serve to distinguish that cleaning tool from those of other users of the appliance, or to distinguish the appliance from other similar appliances. For example, the cleaning tool may form one of a set of similar cleaning tools, where each cleaning tool within the set has a respective different such identifier.

In a ninth aspect, the present invention provides a dental cleaning appliance comprising a handle, a cleaning tool comprising a fluid reservoir for storing a working fluid, the fluid reservoir being at least partially delimited by a transparent external wall and an inner wall, the inner wall bearing an identifier for user identification of the cleaning tool, and a fluid delivery system for receiving working fluid from the fluid reservoir, and for delivering the working fluid to the teeth of a user.

The identifier may be a color. For example, the inner wall may be formed from colored material. Alternatively, the identifier may comprise one or more alphanumeric characters molded or otherwise formed on the inner wall. As mentioned above, the inner wall may be formed from relatively flexible material, and may comprise a diaphragm which is movable relative to the external wall.

The fluid delivery system preferably comprises a cleaning tool conduit system and a handle conduit system. The handle conduit system preferably comprises a fluid inlet for receiving working fluid from the fluid reservoir, and a plurality of conduits for conveying working fluid between the fluid inlet, the pump, the accumulator, the solenoid valve, and a fluid outlet port. The cleaning tool conduit system preferably comprises a fluid inlet port for receiving a burst of working fluid from the handle fluid outlet port, the flexible, or resilient fluid conduit, the pivotable fluid conduit, and the nozzle.

As mentioned above, the cleaning tool is preferably detachably connected to the handle. As the cleaning tool is connected to the handle, the cleaning tool fluid inlet port aligns with the handle fluid outlet port. One of the fluid inlet port and the fluid outlet port may comprise a female fluid connection, and the other one of the fluid inlet port and the fluid outlet port may comprise a male fluid connection, or pipe, which protrudes from a body of the cleaning tool, and which is received by the female fluid connection as the cleaning tool is connected to the handle.

To align the fluid inlet port with the fluid outlet port as the cleaning tool is connected to the handle, the handle preferably comprises a non-rotatable first connector, and the cleaning tool preferably comprises a second connector for connecting with the first connector to connect the handle to the cleaning tool. The first connector is preferably a male connector extending parallel to a longitudinal axis of the handle, and the second connector is preferably a female connector for receiving the male connector. The male connector is preferably in the form of a rod or spigot which protrudes from an external surface of the handle. Alternatively, the second connector may be in the form of a male connector, and the first connector may be in the form of a female connector.

To facilitate alignment of the cleaning tool fluid inlet port with the handle fluid outlet port, each of the male connector and the handle fluid outlet port is preferably radially spaced from the longitudinal axis of the handle. To connect the cleaning tool to the handle, the user visually aligns the cleaning tool longitudinally with the handle, and rotates the cleaning tool relative to the handle, or vice versa, so that the male connector is aligned with the female connector. The male connector is then pushed into the female connector, and simultaneously the cleaning tool fluid inlet port aligns with, or enters, the handle fluid outlet port.

In a tenth aspect, the present invention provides a dental cleaning appliance comprising a cleaning tool, and a handle detachably connected to the cleaning tool, the handle comprising a non-rotatable first connector, and a handle conduit system comprising a handle fluid outlet port spaced from the first connector, each of the first connector and the handle fluid outlet port being located on an end surface of the handle and radially spaced from the longitudinal axis of the handle, the cleaning tool comprising a second connector for connecting with the first connector to connect the handle to the cleaning tool, and a cleaning tool conduit system comprising a cleaning tool fluid inlet port which aligns with the handle fluid outlet port when the cleaning tool is connected to the handle.

The cleaning tool preferably comprises a bristle carrier, a plurality of bristles mounted on the bristle carrier, and a transmission unit connected to the bristle carrier, and the handle preferably comprises a drive unit for driving the transmission unit to move the bristle carrier relative to the handle. The handle preferably comprises a drive unit coupling member for coupling with a transmission unit coupling member located on the cleaning tool. The drive unit coupling member is preferably spaced from each of the longitudinal axis of the handle, the male connector and the handle fluid outlet port. The handle fluid outlet port is preferably angularly spaced from the drive unit coupling member. The handle fluid outlet port is preferably located diametrically opposite to the drive unit coupling member. The male connector is preferably located angularly between, more preferably angularly mid-way between, the handle fluid outlet port and the drive unit coupling member.

The drive unit coupling member is preferably rotatable relative to the handle. Preferably, the drive unit coupling member protrudes from a body of the handle, and is received by the transmission unit coupling member as the cleaning tool is connected to the handle.

The male connector of the handle and the female connector of the cleaning tool preferably form a snap-fit connector for connecting the cleaning tool to the handle.

As discussed above, the appliance may comprise a control circuit for actuating the delivery of working fluid to the teeth of the user depending on the output from a sensor. The sensor is preferably arranged to detect movement of a part of the fluid delivery system relative to the handle. To reduce the risk of undesired ejection of bursts of working fluid when the nozzle is not located within an interproximal gap of the user, for example during handling of the appliance, the appliance preferably has a first operational mode in which the delivery of the burst of working fluid to the teeth of a user is inhibited and a second operational mode in which the burst of working fluid to the teeth of a user is permitted, and wherein, during use of the appliance, the control circuit is arranged to effect a transition between the first operational mode and the second operational mode automatically depending on a detected operational parameter of the appliance.

In an eleventh aspect, the present invention provides a dental cleaning appliance comprising a fluid delivery system for delivering a burst of working fluid to the teeth of a user, and a control circuit for controlling the delivery of the burst of working fluid to the teeth of a user, wherein the appliance has a first operational mode in which the delivery of the burst of working fluid to the teeth of a user is inhibited and a second operational mode in which the burst of working fluid to the teeth of a user is permitted, and wherein, during use of the appliance, the control circuit is arranged to effect a transition between the first operational mode and the second operational mode automatically depending on a detected operational parameter of the appliance.

One of a number of different operational parameters of the appliance may be detected to effect a transition between the operational modes of the appliance. For example, the operational parameter may be one of:

- the activation state (on or off) of the motor for driving the rotation of the bristle carrier;
- the magnitude of the current drawn by the motor;
- the magnitude of a load applied to the appliance during use, such as a force applied to the cleaning tool via the engagements, a force applied to the nozzle, or a force applied to the handle as it is gripped by the user;
- the orientation of the appliance;
- the volume of working fluid in the accumulator; and
- the position of the collar relative to the handle.

The control circuit is preferably arranged to effect a transition between the first operational mode and the second operational mode when the detected operational parameter of the appliance is above a non-zero threshold value.

In addition, or an alternative, to the delivery of a burst of working fluid to the nozzle depending on the output from a sensor, the control circuit may be arranged to actuate the delivery of fluid to the teeth of a user in response to a user action on the appliance. That user action on the appliance may be the actuation of a button of the appliance.

For example, the appliance may have an "automatic" mode, or first mode of fluid delivery, which is selectable by the user and in which a burst of working fluid is delivered to the teeth of a user depending on the output from the sensor. When that mode is not selected by the user, or when a "manual" mode, or a second mode of delivery, is selected by the user, the burst of working fluid is delivered to the user's teeth depending on the user action on the appliance.

Where the cleaning tool comprises a moveable bristle carrier, the detected operational parameter preferably comprises the magnitude of the current drawn by the motor to move the bristle carrier. The drive unit and the transmission unit are preferably arranged to generate a constant speed of movement of the bristle carrier relative to the handle. When the appliance is first activated, or switched on, by the user, the appliance tends not to be in contact with the user's teeth. As a result, the current drawn by the motor tends to be relatively low, and is preferably below a set threshold value so that the appliance is in the first operational mode when first activated.

When the bristles are urged against the teeth of the user, the resistance to the motion of the bristle carrier increases depending on the force with which the bristles are pressed against the teeth. To maintain a constant speed of movement of the bristle carrier, the motor draws an increased amount of current depending on the force applied to the bristle carrier. The control circuit detects the magnitude of the current drawn by the motor, and when that current exceeds a threshold value, which is indicative of the current required to move the bristles against a user's teeth, the control circuit effects the transition to the second operational mode. When the detected current falls below that threshold value, the control circuit effects a transition back to the first operational mode.

As mentioned above, the nozzle is preferably moveable between a proximal position and a distal position. In the distal position, the tip of the nozzle is preferably proud of at least some of the free ends of the bristles. As the bristles are pressed against a user's teeth, the bristles will deflect, reducing the direct spacing between the ends of the bristles and the bristle carrier and, simultaneously, moving the tip of the nozzle towards the bristle carrier, and so towards its proximal position. Depending on how far the bristles bend during use, and thus on the stiffness of the bristles, the movement of the nozzle relative to the head can be detected from the variation of the output received from the sensor, and used as an indicator of the load being applied to the head during use of the appliance. This can be particularly useful when the bristles are mounted on a static bristle carrier, or directly to the head of the appliance.

In a twelfth aspect, the present invention provides a dental cleaning appliance comprising a handle, a cleaning tool connected to the handle, part of the cleaning tool being moveable relative to the handle as the cleaning tool is moved along a user's teeth, said part of the cleaning tool being moveable about a first axis, an arm having a first end which is connected to said part of the cleaning tool for movement therewith, and a second end which is remote from the first end, the arm being pivotably moveable relative to said part of the cleaning tool about a second axis which is spaced from the first axis, and a sensor for generating an output which varies depending on the relative positions of the sensor and the second end of the arm.

As mentioned above, the cleaning tool is preferably detachably connected to the handle. This can allow a handle to be provided with a set of similar cleaning tools, each with a respective different identifier. This can also allow a handle to be provided with a set of dissimilar cleaning tools. For example, the set of cleaning tools may be selected from two or more of a first type of cleaning tool with a nozzle and a moveable brush unit, a second type of cleaning tool with a nozzle and a static brush unit, a third type of cleaning tool with a nozzle and no bristles, and a fourth type of cleaning tool with a moveable brush unit and no nozzle. A number of respective different cleaning tools of the same type may also be provided, for example, of the first type of cleaning tool, with bristles having a respective different stiffness, or with nozzles having respective different fluid outlet sizes.

The appliance is preferably a handheld appliance which includes all of the aforementioned components of the appliance.

The cleaning tools may be sold as stand-alone items, for example as spare parts or as alternative cleaning tools for use with an existing handle.

In a thirteenth aspect, the present invention provides a cleaning tool for a dental cleaning appliance comprising a handle to which the cleaning tool is detachably connectable, the cleaning tool comprising a stem, and a cleaning tool conduit system comprising a nozzle for delivering a burst of working fluid to the teeth of a user, and a moveable fluid conduit which is moveable relative to the stem, the nozzle being moveable with the fluid conduit, the fluid conduit being biased for movement in a direction which urges the nozzle against a user's teeth during use of the appliance.

In a fourteenth aspect, the present invention provides a cleaning tool for a dental cleaning appliance comprising a handle to which the cleaning tool is detachably connectable, the handle comprising a drive unit, the drive unit comprising a motor and a drive unit coupling member, the cleaning tool comprising a cleaning tool fluid conduit system comprising a nozzle for delivering a burst of working fluid to the teeth of a user, a brush unit comprising a bristle carrier and a plurality of bristles mounted on the bristle carrier, the brush unit extending about the nozzle, and a transmission unit connected to the bristle carrier for moving the bristle carrier relative to the nozzle, the transmission unit comprising a transmission unit coupling member for coupling with the drive unit transmission unit when the cleaning tool is connected to the handle.

In a fifteenth aspect, the present invention provides a cleaning tool for a dental cleaning appliance comprising a handle to which the cleaning tool is detachably connectable, the cleaning tool comprising a stem, a nozzle for delivering the burst of working fluid to the teeth of a user, and a fluid reservoir for storing working fluid, the fluid reservoir being connected to and extending around the stem.

In a sixteenth aspect, the present invention provides a cleaning tool for a dental cleaning appliance comprising a handle to which the cleaning tool is detachably connectable, the cleaning tool comprising a stem, a fluid reservoir for storing a working fluid, and an external collar comprising a fluid port, the collar being moveable relative to the stem between a first position in which, when the cleaning tool is connected to the handle, the fluid port is exposed to allow the fluid reservoir to be replenished, and a second position in which, when the cleaning tool is connected to the handle, the fluid port is occluded.

In a seventeenth aspect, the present invention provides a cleaning tool for a dental cleaning appliance comprising a handle to which the cleaning tool is detachably connectable, the handle comprising a handle conduit system, the cleaning tool comprising a fluid reservoir for supplying a working fluid to the handle conduit system, the fluid reservoir being at least partially delimited by a wall and a movable member which is moveable relative to the wall to vary the volume of the fluid reservoir, a cleaning tool conduit system for receiving a burst of working fluid from the handle conduit system and for delivering the burst of working fluid to the teeth of a user, and an expansion chamber located adjacent to the moveable member and which increases in volume as the volume of the fluid reservoir decreases as working fluid is supplied to the handle conduit system.

The handle of the appliance may also be provided separately from the cleaning tool, for example as a spare part for the appliance, or for use by a different user. For example, handles having respective different shapes may be provided for use by users of different age.

In an eighteenth aspect, the present invention provides a handle for a dental cleaning appliance comprising a cleaning tool to which the handle is detachably connectable, the cleaning tool comprising a nozzle through which a burst of working fluid is delivered to the teeth of a user, the handle comprising a fluid inlet, a pump for drawing working fluid through the fluid inlet, a hydraulic accumulator for receiving working fluid from the pump, a fluid outlet which is in fluid communication with the nozzle when the cleaning tool is connected to the handle, a valve located between the accumulator and the fluid outlet, the valve having an open position for enabling the accumulator to deliver a burst of working fluid to the fluid outlet and a closed position for enabling the accumulator to be replenished under the action of the pump, and a control circuit for controlling the position of the valve.

In a nineteenth aspect, the present invention provides a handle for a dental cleaning appliance comprising a cleaning tool to which the handle is detachably connectable, the cleaning tool comprising a fluid reservoir for storing a working fluid, and a moveable collar having a fluid port in fluid communication with the fluid reservoir, the handle comprising a body comprising a recessed portion for exposing the fluid port when the cleaning tool is connected to the handle and the collar is in a first position relative to the body, and a handle conduit system comprising a fluid inlet for receiving working fluid from the fluid reservoir when the cleaning tool is connected to the handle and the collar is in a second position relative to the body.

One or more of the aforementioned aspects of the invention may also be applied more generally to cleaning apparatus or a cleaning appliance. The apparatus may be a surface treating appliance. For example, the apparatus may be in the form of apparatus, preferably a handheld apparatus, for cleaning a work surface, in which the brush unit is arranged to engage a work surface and the nozzle is arranged to deliver cleaning fluid to the work surface during cleaning.

In a twentieth aspect, the present invention provides a surface treating appliance comprising a handle, a fluid delivery system comprising a nozzle for delivering a burst of working fluid to a surface, a brush unit for engaging the surface, the brush unit comprising a bristle carrier and a plurality of bristles mounted on the bristle carrier, the brush unit extending at least partially about the nozzle, and a drive unit for driving movement of the bristle carrier relative to the nozzle.

In a twenty first aspect, the present invention provides a surface treating appliance comprising a fluid delivery system comprising a fluid inlet, a pump for drawing a working fluid through the fluid inlet, a hydraulic accumulator for receiving working fluid from the pump, a nozzle having a fluid outlet, and a valve located between the accumulator and the nozzle, the valve having an open position for enabling the accumulator to deliver a burst of working fluid to the nozzle and a closed position for enabling the accumulator to be replenished under the action of the pump, and a control circuit for actuating the pump, and for controlling the position of the valve.

In a twenty second aspect, the present invention provides a surface treating appliance comprising a handle and a cleaning tool detachably connected to the handle, the cleaning tool comprising a nozzle for delivering a burst of working fluid to a surface, a stem extending between the handle and the nozzle, and a fluid reservoir for storing working fluid, the fluid reservoir being connected to and extending around the stem.

In a twenty third aspect, the present invention provides a surface treating appliance comprising a handle, a fluid reservoir for storing a working fluid, a fluid delivery system for receiving working fluid from the fluid reservoir, and for delivering a burst of working fluid to a surface, and an external collar comprising a fluid port, the collar being moveable relative to the handle between a first position in which the fluid port is exposed to allow the fluid reservoir to be replenished, and a second position in which the fluid port is occluded.

In a twenty fourth aspect, the present invention provides a surface treating appliance comprising a handle, a fluid reservoir for storing a working fluid, the fluid reservoir being at least partially delimited by a wall and a movable member which is moveable relative to the wall to vary the volume of the fluid reservoir, a fluid delivery system for receiving working fluid from the fluid reservoir, and for delivering the working fluid to a surface, and an expansion chamber located adjacent to the moveable member and which increases in volume as the volume of the fluid reservoir decreases as working fluid is supplied to the fluid delivery system.

Features described above in connection with the first aspect of the invention are equally applicable to each of the second to twenty fourth aspects of the invention, and vice versa.

BRIEF DESCRIPTION OF THE DRAWINGS

Preferred features of the present invention will now be described by way of example only with reference to the accompanying drawings, in which:

FIGS. 14(a) and 14(b) are sectional views of a spring-type accumulator of the fluid delivery system, with a fluid chamber of the accumulator in empty and full configurations respectively;

FIGS. 15(a) and 15(b) are sectional views of an alternative gas-charged accumulator of the fluid delivery system, with a fluid chamber of the accumulator in empty and full configurations respectively;

FIG. 16(a) is a sectional view of a solenoid valve of the fluid delivery system, and FIG. 16(b) is an exploded sectional view of the solenoid valve;

FIG. 19(a) is a side view of the assembly of FIG. 18(d) with the nozzle in a distal position relative to the cleaning tool, and FIG. 19(b) is a similar view to FIG. 19(a) with the nozzle in a proximal position relative to the cleaning tool;

FIG. 20 illustrates the replenishment of the fluid reservoir with working fluid.

DETAILED DESCRIPTION OF THE INVENTION

Figures 1A, 1B, 1C:
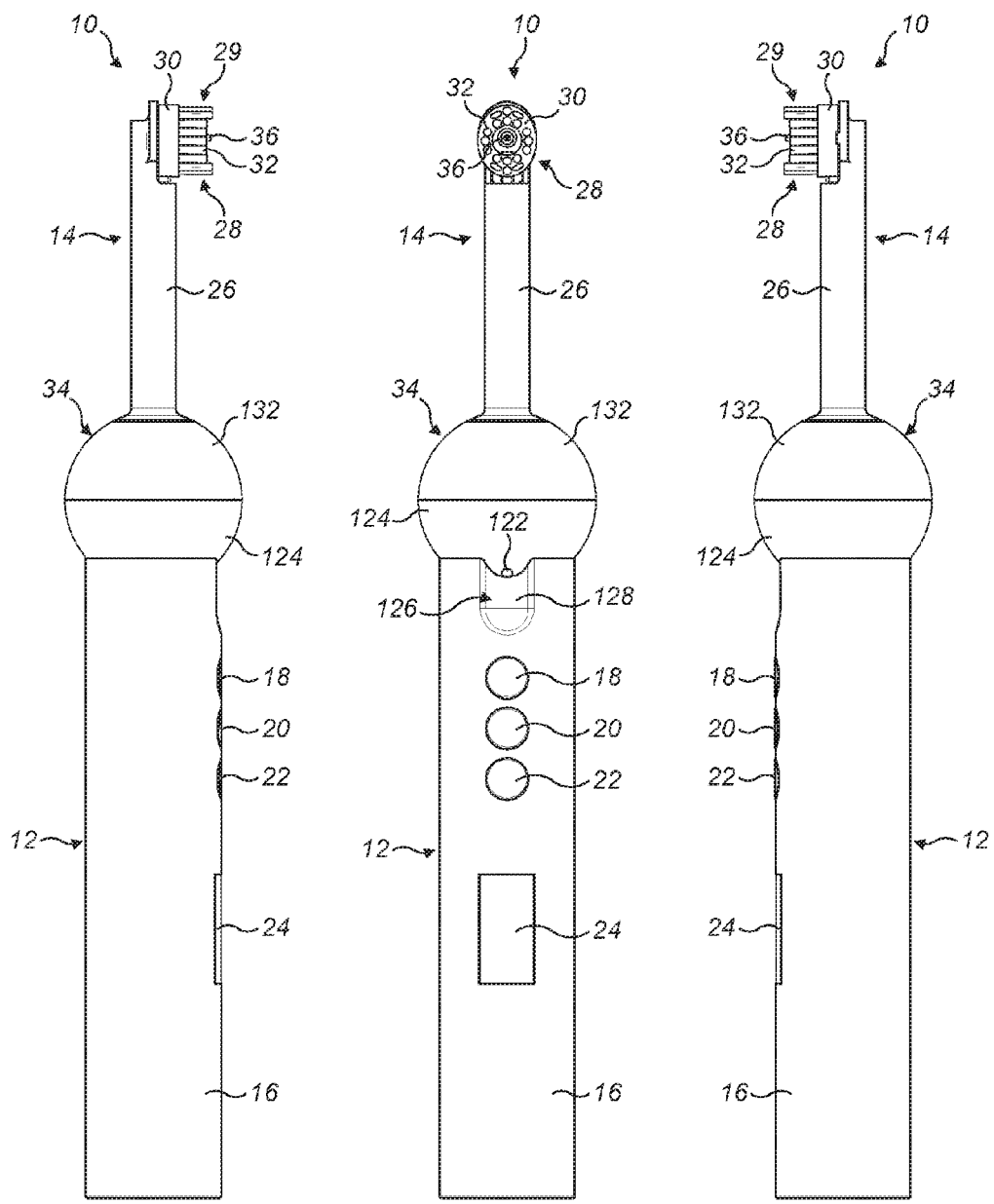
FIG. 1(a) is a right side view of a dental cleaning appliance.
FIG. 1(b) is a front view of the appliance.
FIG. 1(c) is a left side view of the appliance.
Figure 2A:
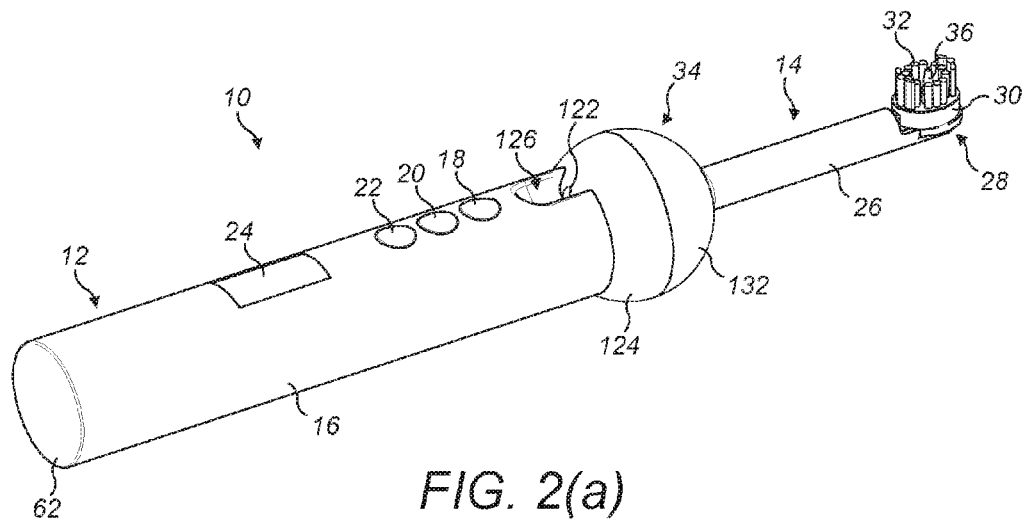
FIG. 2(a) is a left side perspective view, for above, of the appliance.
Figure 2B:
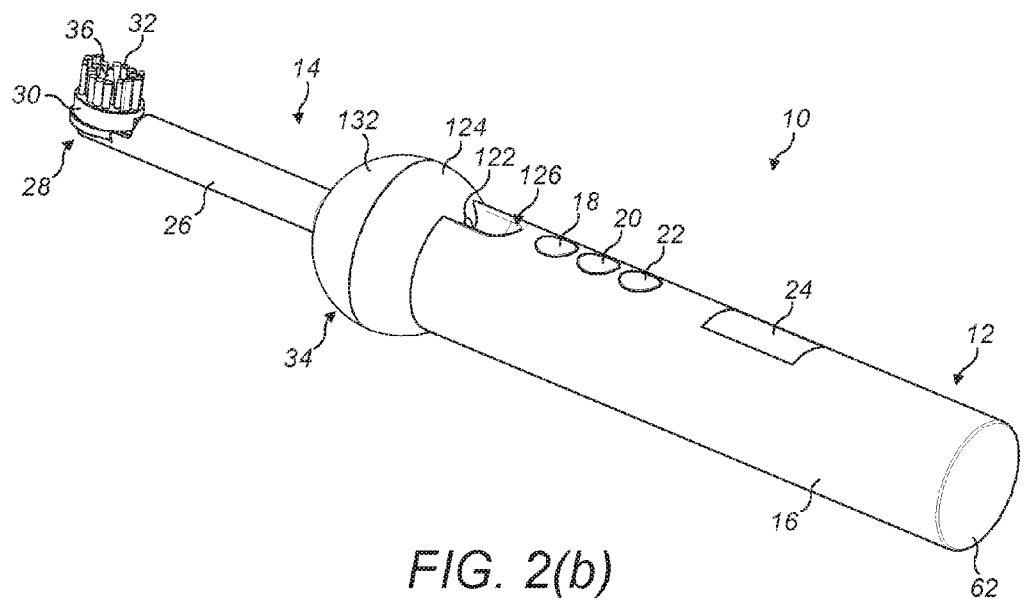
FIG. 2(b) is a right side perspective view, from above, of the appliance.

FIGS. 1 and 2 illustrate external views of an embodiment of a dental cleaning appliance 10. In this embodiment, the appliance is in the form of a handheld appliance, which is in the form of an electric toothbrush having an integrated assembly for dispensing a working fluid for improved interproximal cleaning.

The appliance 10 comprises a handle 12 and a cleaning tool 14. The handle 12 comprises an external body 16 which is gripped by a user during use of the appliance 10. The body 16 is preferably formed from plastics material, and is preferably generally cylindrical in shape. The handle 12 comprises a plurality of user operable buttons 18, 20, 22 which are located within respective apertures formed in the body 16 so as to be accessible to the user. The handle 12 further comprises a display 24 which is positioned so as to be visible to a user during use of the appliance. In this embodiment, the display 24 is also located within a respective aperture formed in the body 16.

The cleaning tool 14 comprises a stem 26 and a head 28. The stem 26 is elongate in shape, which serves to space the head 28 from the handle 12 to facilitate user operability of the appliance 10. The head 28 comprises a brush unit 29, which comprises a bristle carrier 30 and a plurality of bristles 32 mounted on the bristle carrier 30. As discussed in more detail below, the bristle carrier 30 is moveable relative to the stem 26 and the handle 12. The cleaning tool 14 also comprises a fluid reservoir 34 for storing a working fluid, and a nozzle 36 for delivering one or more bursts of working fluid to the teeth of the user during use of the appliance 10. The fluid reservoir 34 is connected to the stem 26. The fluid reservoir 34 extends at least partially around the stem 26. The brush unit 29 extends at least partially around the nozzle 36. The fluid reservoir 34 and the nozzle 36 are also discussed in more detail below.

Figure 3:
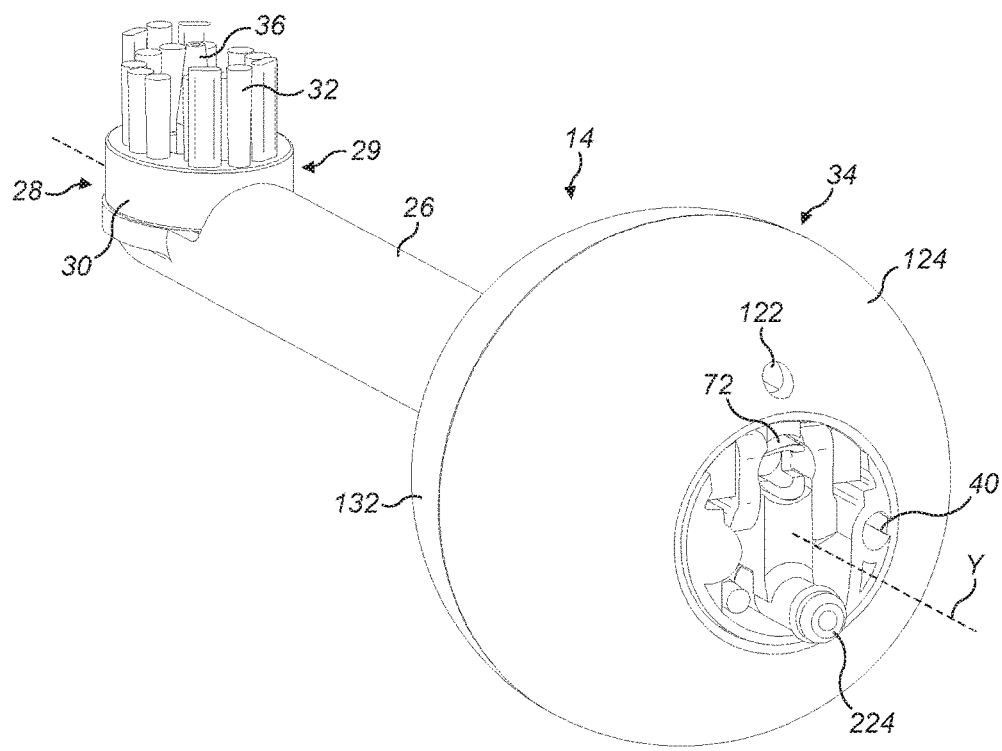
FIG. 3 is a right side perspective view, from above, of a cleaning tool of the appliance.
Figure 4:
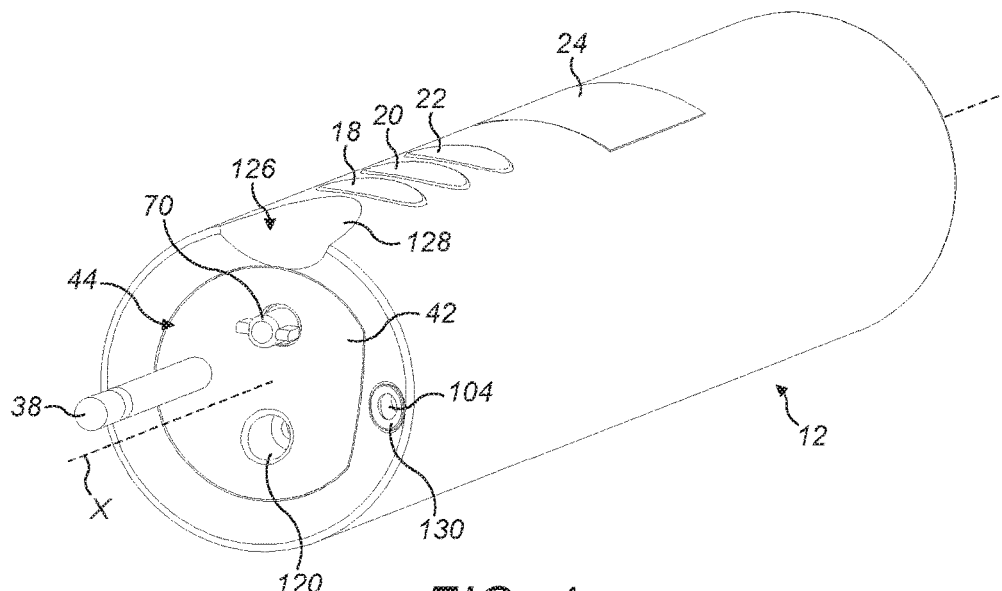
FIG. 4 is a right side perspective view, from above, of a handle of the appliance.
Figure 5:
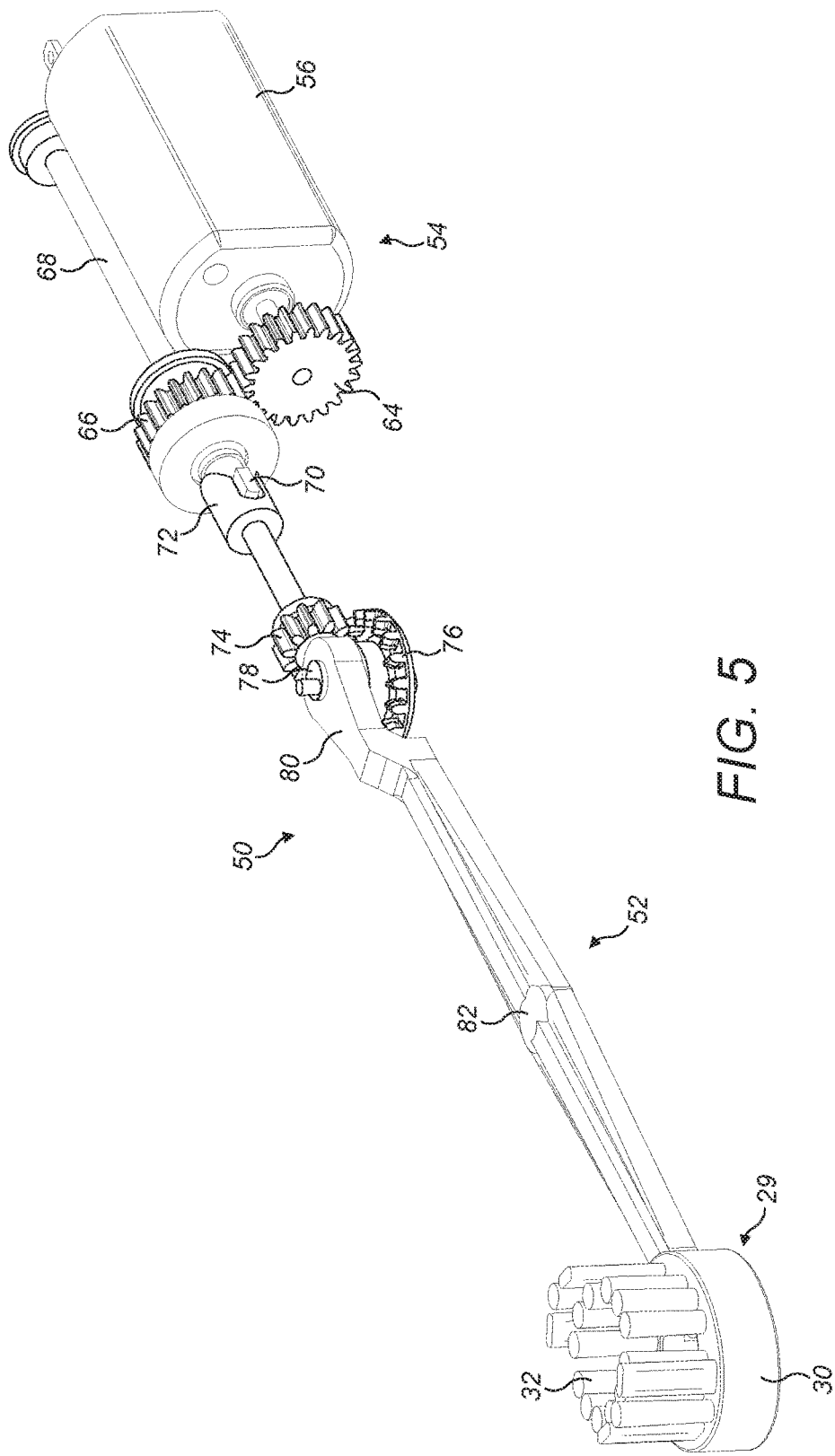
FIG. 5 is a perspective view of a drive mechanism for driving the movement of a brush unit relative to the handle.
Figure 6:
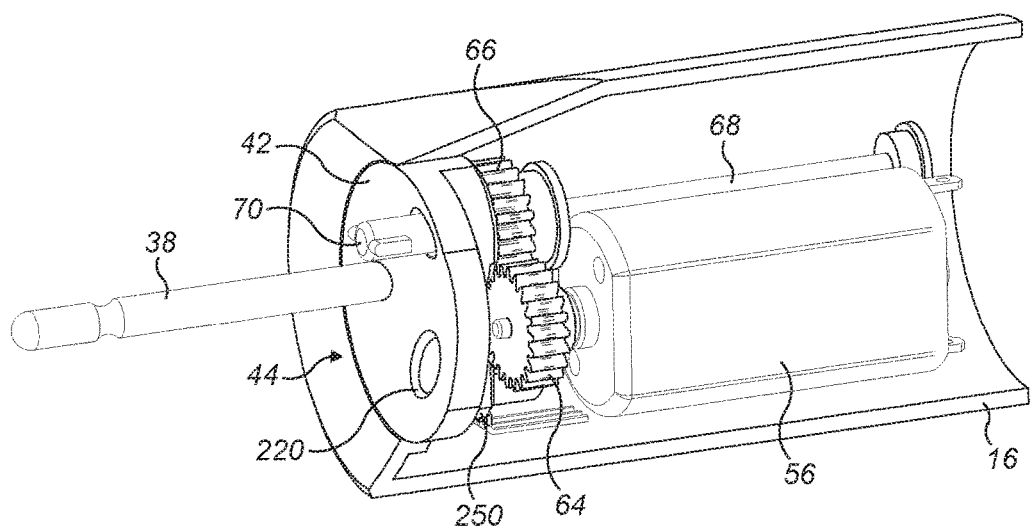
FIG. 6 is a cutaway view of part of the handle.
Figure 7A:
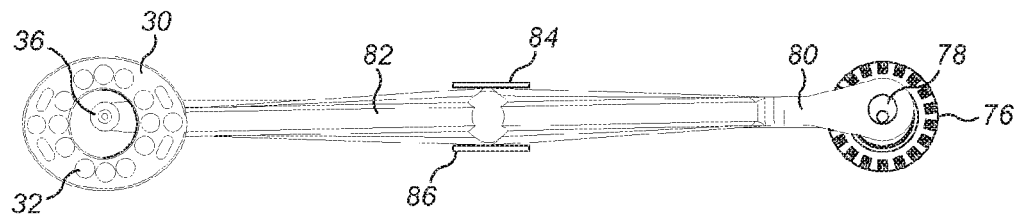
FIGS. 7(a) to 7(d) is a series of views which illustrate the movement of the brush unit, and a transmission unit of the drive mechanism, relative to the handle.
Figure 7B:
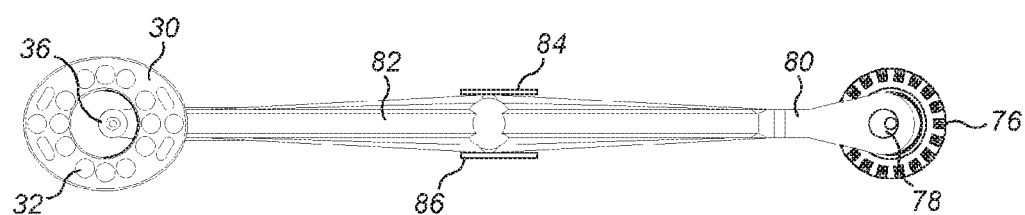
Figure 7C:
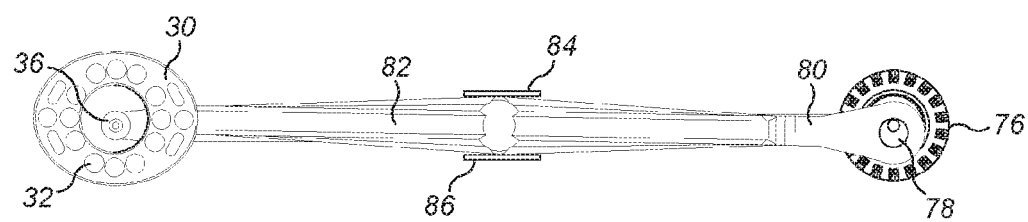
Figure 7D:
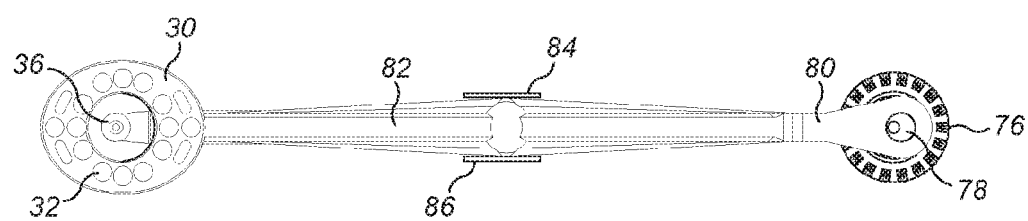

The cleaning tool 14 is detachably connected to the handle 12. With reference to FIGS. 3 and 4, the handle 12 comprises a male connector 38, preferably in the form of a pin or spigot, which is received by a complementary female connector 40, preferably in the form of a recess, of the cleaning tool 14. The male connector 38 preferably protrudes outwardly from a concave end surface 42 of the body 16, and preferably in a direction which is parallel to the longitudinal axis X of the handle 12. The end surface 42 defines a recess for receiving a convex end surface of the cleaning tool 14 so that, as illustrated in FIGS. 1 to 3, part of the outer surface of the cleaning tool 14 is occluded or covered by the handle 12 when the cleaning tool 14 is connected to the handle 12.

The male connector 38 is radially spaced from the longitudinal axis X of the handle 12, and the female connector 40 is similarly spaced from the longitudinal axis Y of the cleaning tool 14. To connect the cleaning tool 14 to the handle 12, the user visually aligns the longitudinal axis X of the handle 12 with the longitudinal axis Y of the cleaning tool 14, and angularly aligns the connectors 38, 40 before pushing the cleaning tool 14 towards the handle 12 to insert the male connector 38 into the female connector 40. The connectors 38, 40 preferably form a snap-fit connection when the male connector 38 has been inserted fully into the female connector 40. The connectors 38, 40 may be subsequently disconnected by pulling apart the handle 12 and the cleaning tool 14.

As mentioned above, the cleaning tool 14 includes a bristle carrier 30 which is moveable relative to the stem 26. With reference also to FIGS. 5 to 8, the appliance 10 comprises a drive mechanism 50 for driving the movement of the bristle carrier 30 relative to the stem 26. The drive mechanism 50 comprises a transmission unit 52 connected to the bristle carrier 30, and a drive unit 54 for driving the transmission unit 52 to move the bristle carrier 30 relative to the stem 26.

Figure 10:
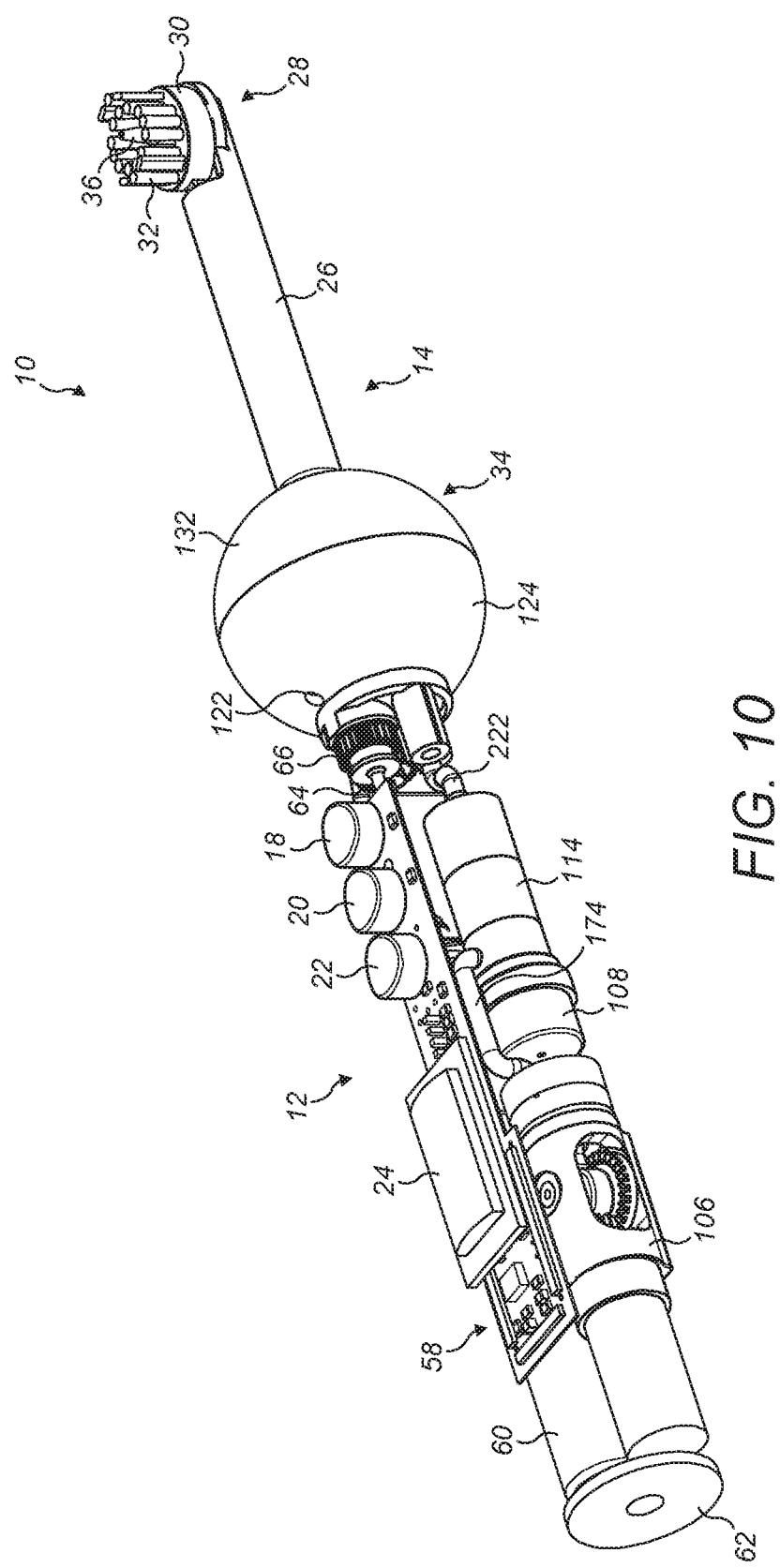
FIG. 10 is a similar view to FIG. 2(a), but with the outer body of the handle removed.

The handle 12 comprises the drive unit 54 of the drive mechanism 50. The drive unit 54 comprises a motor 56, preferably in the form of a dc motor, which is actuated by a control circuit 58 (shown in FIG. 10) in response to the user depression of one or more of the buttons of the handle 12, as described below. The motor 56 is powered by a battery 60 (also shown in FIG. 10) located within the handle 12. The battery 60 may be a non-rechargeable battery which may be accessed for replacement by the user via a removable cover 62 located in the base of the handle 12. Alternatively, the battery 60 may be a rechargeable battery, which may be charged as required by the user using a wireless battery charger, as is known.

The motor 56 is connected to a gear train located within the handle 12. The gear train comprises a first spur gear 64 connected to a rotary shaft of the motor 56, and a second spur gear 66 which meshes with the first spur gear 64 and is supported by a shaft 68 for rotation about an axis which is generally parallel with the rotational axis of the motor 56. The second spur gear 66 is connected to a drive unit coupling member 70 which protrudes outwardly from the end surface 42 of the body 16, and which rotates relative to the body 16 upon actuation of the motor 56. The drive unit coupling member 70 is also spaced from the longitudinal axis X of the handle 12, and is preferably angularly spaced from the male connector 38.

The cleaning tool 14 comprises the transmission unit 52 of the drive mechanism 50. The transmission unit 52 comprises a transmission unit coupling member 72 which couples with, and preferably receives, the drive unit coupling member 70 when the cleaning tool 14 is connected to the handle 12. The transmission unit coupling member 72 is connected to a gear train located in the cleaning tool 14. The gear train comprises a first contrate gear 74 which is connected to the transmission unit coupling member 72, and a second contrate gear 76 which meshes at a right angle with the first contrate gear 74 so that the second contrate gear 76 rotates about an axis which is orthogonal to the longitudinal axis Y of the cleaning tool 14.

A crank 78 is connected to the second contrate gear 76 such that the axis of the crank 78 is spaced from the rotational axis of the second contrate gear 76. With rotation of the second contrate gear 76, the crank 78 moves in a circular orbital path centred on the rotational axis of the second contrate gear 76. A first end 80 of an elongate connecting rod 82 is connected to the crank 78 for movement with the crank 78 about the rotational axis of the second contrate gear 76. The connecting rod 82 is housed within the stem 26. The other end of the connecting rod 82 is connected to the side surface of the bristle carrier 30. Lateral movement of the connecting rod 82 relative to the stem 26 is constrained by a pair of parallel guide members 84, 86 connected to the stem 26, and which each engage a respective side surface of the connecting rod 82, and so that orbital movement of the crank 78 results in orbital movement of the bristle carrier 30 about a circular orbital path relative to the stem 26.

Figure 8A:
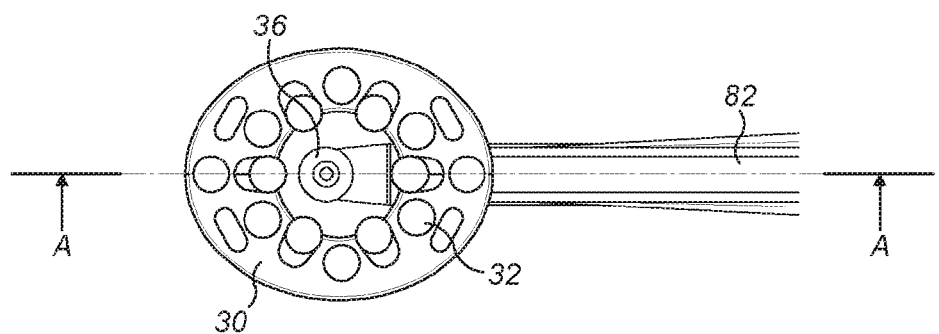
FIG. 8(a) is a top view of the head of the cleaning tool.
Figure 8B:
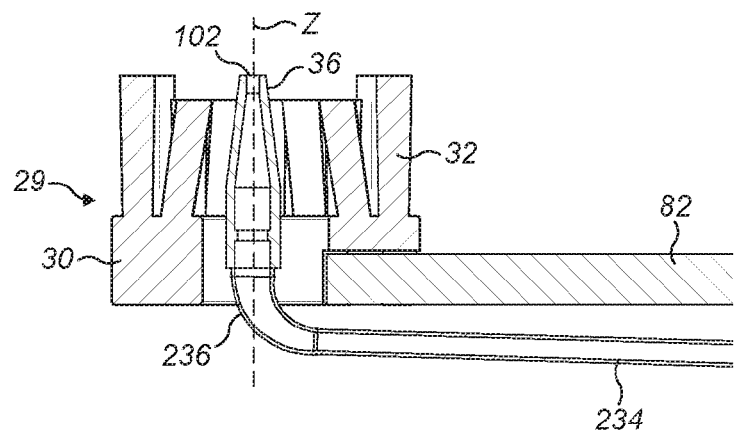
FIG. 8(b) is a sectional view of the head taken along line A-A in FIG. 8(a)

As mentioned above, the brush unit 29, which comprises the bristle carrier 30 and the bristles 32, extends at least partially around the nozzle 36. In this embodiment, the bristle carrier 30 surrounds the nozzle 36. As shown in FIGS. 7 and 8, the bristle carrier 30 is annular in shape, and is preferably spaced from the nozzle 36 so that the bristle carrier 30 moves relative to the nozzle 36. The orbital path of the bristle carrier 30 is preferably generally centred on the nozzle 36. The radius of the orbital path is preferably in the range from 0.5 to 1 mm.

Figure 9:
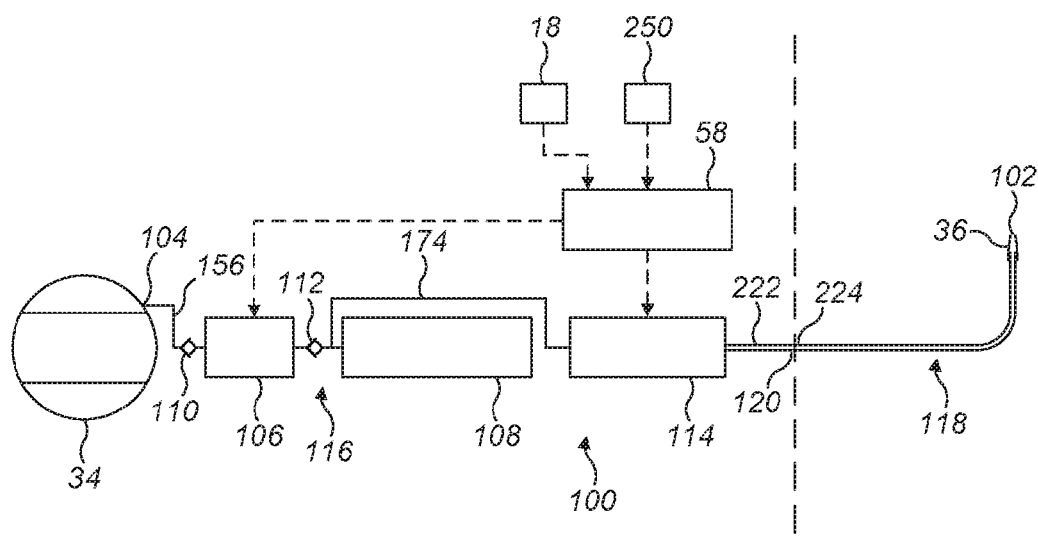
FIG. 9 illustrates schematically components of a fluid delivery system for delivering a burst of a working fluid to the teeth of a user, and a control system for controlling the fluid delivery system.

The nozzle 36 forms part of a fluid delivery system 100 for receiving working fluid from the fluid reservoir 34 and for delivering bursts of working fluid to the teeth of a user during use of the appliance 10. The tip of the nozzle 36 comprises a fluid outlet 102 through which a burst of working fluid is delivered to the teeth of the user. The fluid delivery system 100 is illustrated schematically in FIG. 9. In overview, the fluid delivery system 100 comprises a fluid inlet 104 for receiving working fluid from the fluid reservoir 34. In this embodiment, the working fluid is a liquid working fluid, which is preferably water. The fluid delivery system 100 comprises a pump 106 for drawing working fluid from the fluid reservoir 34 through the fluid inlet 104, and for delivering the working fluid to a hydraulic accumulator 108. A first one-way valve 110 is located between the fluid inlet 104 and the pump 106, and a second one-way valve 112 is located between the pump 106 and the accumulator 108. A solenoid valve 114 is located downstream from the accumulator 108. The control circuit 58 controls the movement of the solenoid valve 114 between a closed position, which is adopted when working fluid is being delivered to the accumulator 108 by the pump 106, and an open position, which is adopted to effect the delivery of a burst of working fluid from the accumulator 108 to the nozzle 36.

The fluid inlet 104, the pump 106, the accumulator 108 and the solenoid valve 114 are located in the handle 12. In other words, a first part of the fluid delivery system 100 is located in the handle 12, and a second part of the fluid delivery system 100 is located in the cleaning tool 14. The fluid delivery system 100 thus comprises a handle conduit system 116 which is located in the handle 12, and a cleaning tool conduit system 118 which is located in the cleaning tool 14. With reference also to FIGS. 3 and 4, the fluid inlet 104 provides a fluid inlet of the handle conduit system 116, and a handle fluid outlet port 120 provides a fluid outlet of the handle conduit system 116.

The fluid reservoir 34 is connected to, and extends at least partially around, the stem 26 of the cleaning tool 14. In this embodiment, the fluid reservoir 34 is annular in shape, and so surrounds the stem 26. The fluid reservoir 34 is preferably located at or towards the end of the stem 26 which is remote from the head 28. The fluid reservoir 34 preferably has a capacity in the range from 5 to 50 ml, and in this embodiment has a capacity of 25 ml.

The fluid inlet 104 is arranged to receive working fluid from the fluid reservoir 34, and so in this embodiment the fluid inlet 104 is located on the concave end surface 42 of the body 16 of the handle 12. With reference to FIGS. 10 to 12(c), working fluid is supplied to the fluid inlet 104 of the handle conduit system 116 from a fluid port 122 which is in fluid communication with the fluid reservoir 34. The fluid port 122 is located on an external collar 124 of the cleaning tool 14. The collar 124 is moveable relative to both the handle 12 and the stem 26 of the cleaning tool 14. In this embodiment, the collar 124 is rotatable relative to the handle 12 about the longitudinal axis Y of the cleaning tool 14. To move the collar 124 relative to the handle 12, the user grasps the handle 12 with one hand, and, with the other hand, turns the collar 124 about the longitudinal axis Y in the desired angular direction.

Figure 11A:
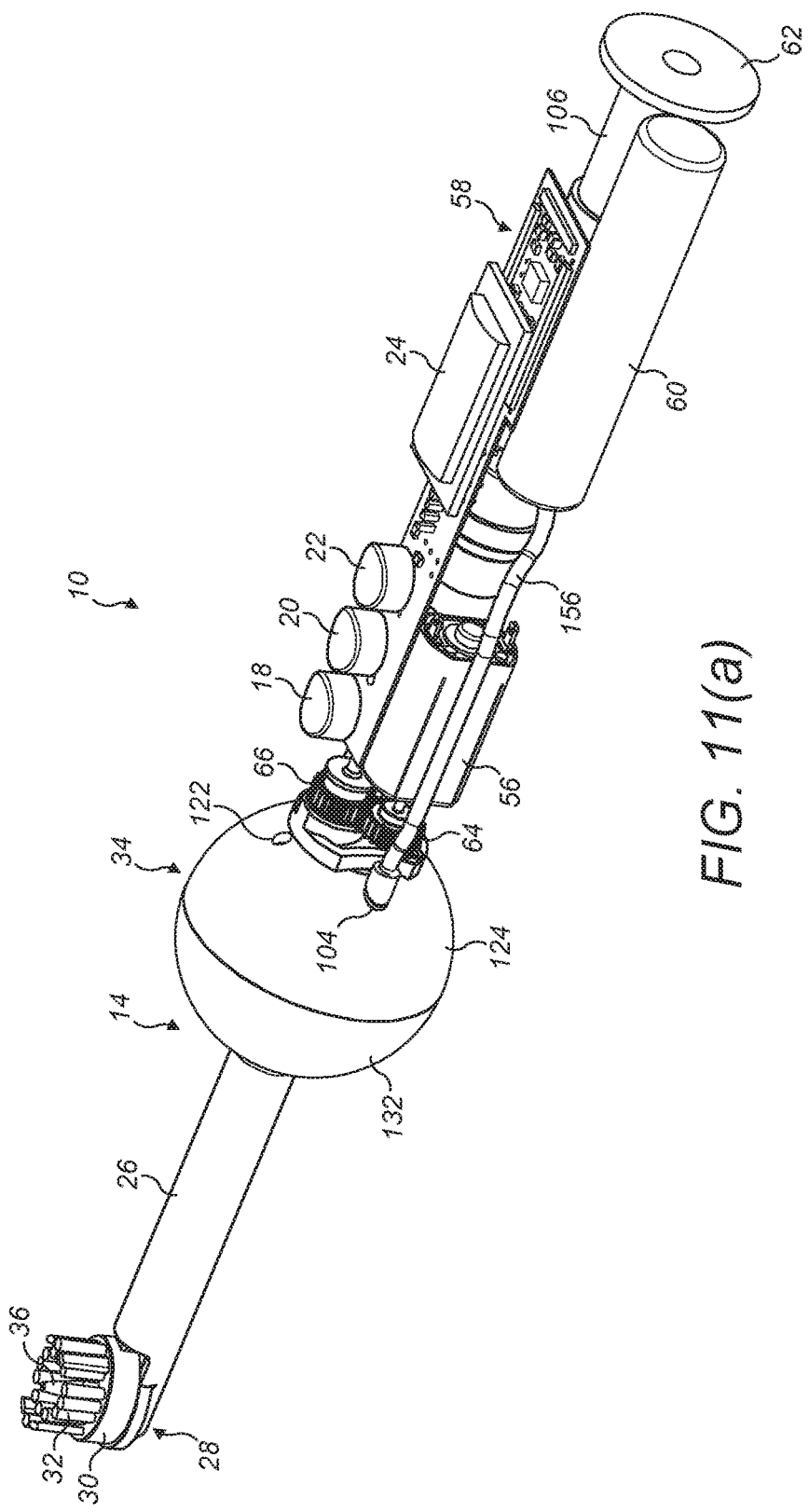
FIG. 11(a) is a similar view to FIG. 2(b), but with the outer body of the handle removed and with a collar of the cleaning tool in a first position relative to the handle.
Figure 11B:
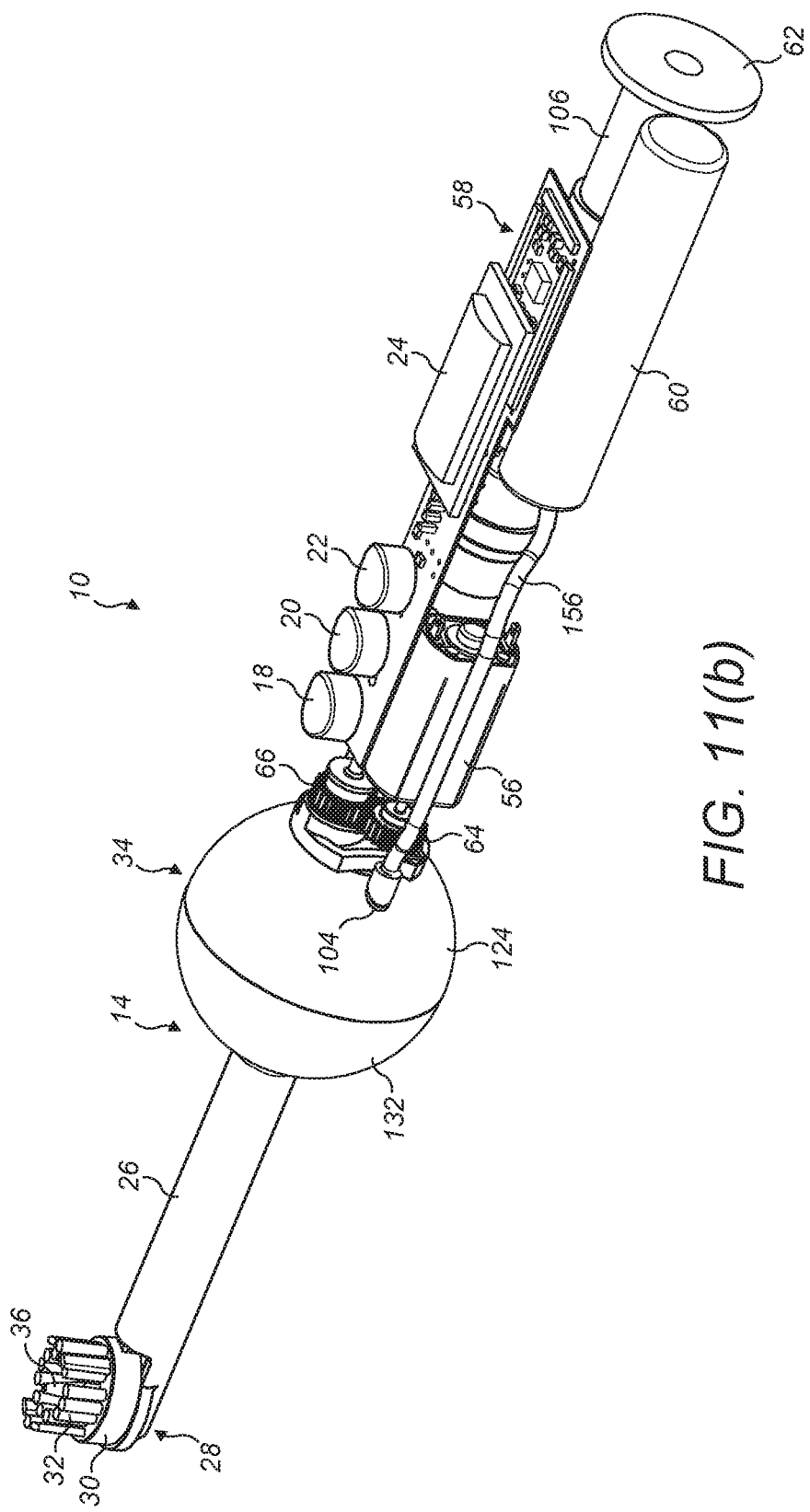
FIG. 11(b) is a similar view to FIG. 11(a), but with the collar in a second position relative to the handle.

The collar 124 is moveable relative to the handle 12 between a first position, as illustrated in FIG. 11(a), and a second position, as illustrated in FIG. 11(b). The second position is angularly spaced from the first position, preferably by an angle in the range from 60 to 180°, and in this embodiment by an angle of around 90°.

When the collar 124 is in the first position relative to the handle 12, as also illustrated in FIGS. 1 to 3 and 10, the fluid port 122 is exposed to allow the fluid reservoir 34 to be replenished by the user. The fluid port 122 is exposed by a recessed portion 126 of the body 16 of the handle 12. The recessed portion 126 comprises a curved wall 128. The curved wall 128 is shaped so that, during filling or replenishment of the fluid reservoir 34 by the user, working fluid is guided towards the exposed fluid port 122.

When the collar 124 is in the second position relative to the handle 12, the fluid port 122 is occluded by the handle 12 so that the fluid port 122 is not accessible by the user. As the fluid port 122 also serves to supply working fluid to the handle conduit system 116, in the second position the fluid port 122 is placed in fluid communication with the fluid inlet 104. The end surface 42 of the body 16 comprises an annular seal, or O-ring, 130 which extends about the fluid inlet 104. When the collar 124 is in the second position, the seal 130 engages an annular portion of the surface of the collar 124 which surrounds the fluid port 122 to inhibit leakage of working fluid from the fluid reservoir 34. One or more stop members may be provided on one, or both, of the fluid reservoir 34 and the handle 12 to inhibit the movement of the collar 124 beyond the first position and the second position.

The collar 124 may be spaced from the fluid reservoir 34, but in this embodiment the collar 124 forms part of an external wall 132 of the fluid reservoir 34. The external wall 132 of the fluid reservoir 34 is thus moveable relative to the handle 12 and the stem 26 of the cleaning tool 14. The external wall 132 is preferably transparent to allow a user to observe the contents of the fluid reservoir 34, and so assess whether the fluid reservoir 34 requires replenishment prior to the desired use of the appliance 10.

The external wall 132 of the fluid reservoir 34 extends around the stem 26 of the cleaning tool 14. The external wall 132 preferably has a shape which is symmetrical about the longitudinal axis Y of the cleaning tool 14. The external wall 132 preferably has a curved shape, more preferably a convex curved shape, but alternatively the external wall 132 may have a polygonal or faceted shape. In this embodiment, the external wall 132 has a spherical curvature. The external wall 132 has diametrically opposed circular apertures 134, 136 which are centred on the longitudinal axis Y of the cleaning tool 14 to allow the stem 26 of the cleaning tool 14 to pass therethrough.

The fluid reservoir 34 further comprises an inner wall 138 which is connected to the external wall 132. The external wall 132 and the inner wall 138 together define the capacity of the fluid reservoir 34. The inner wall 138 is tubular in shape, and also surrounds the stem 26 of the cleaning tool 14. The ends 140, 142 of the inner wall 138 are preferably circular in shape, and are connected to the external wall 132 so as to form a fluid-tight seal between the external wall 132 and the inner wall 138.

The inner wall 138 thus moves with the external wall 132 as the collar 124, which in this embodiment forms part of the external wall 132, moves relative to the handle 12. The entire fluid reservoir 34 may be considered to be moveable relative to the handle 12 as the collar 124 is moved between its first and second positions relative to the handle 12.

The inner wall 138 has an external surface 144 which faces the external wall 132 of the fluid reservoir 34. As the inner wall 138 is visible to the user through the external wall 132, the external surface 144 of the inner wall 138 may bear an identifier for user identification of the cleaning tool 14. For example, the identifier may be a coloured portion of the external surface 144 of the inner wall 138, or one or more alphanumeric characters moulded or otherwise formed on the external surface 144 of the inner wall 138.

Figure 12A:
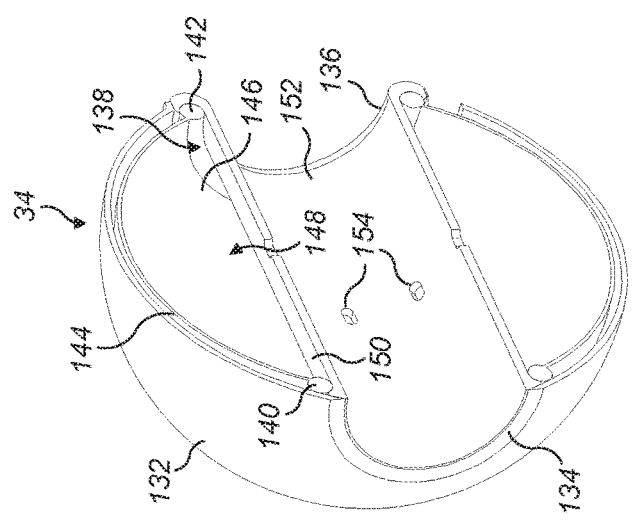
FIG. 12(a) is a sectional view of a fluid reservoir of the cleaning tool, and with a diaphragm of the fluid reservoir in a fully contracted configuration.

FIG. 12(a) illustrates the fluid reservoir 34 when it has been filled with working fluid. In this embodiment, the external wall 132 is formed from relatively rigid material, and the inner wall 138 is formed from relatively flexible material. The thickness of the inner wall 138, and the material from which the inner wall 138 is formed, are selected so that at least part of the inner wall 138 is moveable relative to the external wall 132 in response to a pressure differential which is established across the inner wall 138 as working fluid is drawn from the fluid reservoir 34 by the pump 106. In this embodiment, the inner wall 138 is in the form of a diaphragm or bladder which has ends 140, 142 secured to the external wall 132, and which is expandable in response to a pressure differential which is generated across the surfaces 144, 146 of the inner wall 138 as working fluid is drawn from the fluid reservoir 34. FIG. 12(a) illustrates the inner wall 138 in a fully contracted configuration, or state, in which the capacity of the fluid reservoir 34 is maximised.

Figure 12B:
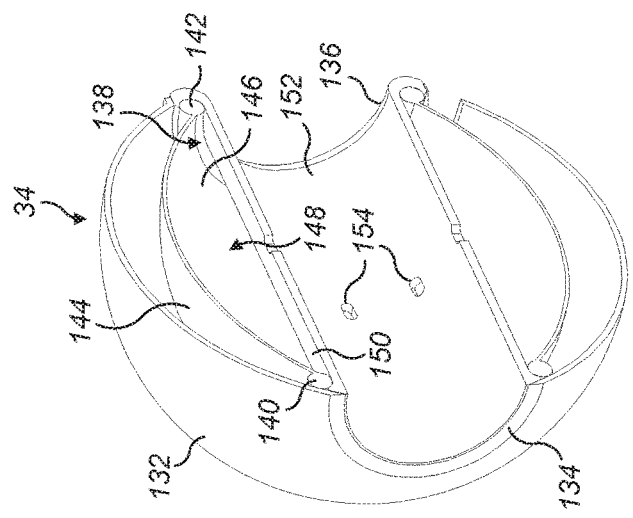
FIG. 12(b) is a similar view to FIG. 12(a) but with the diaphragm in a partially expanded configuration.
Figure 12C:
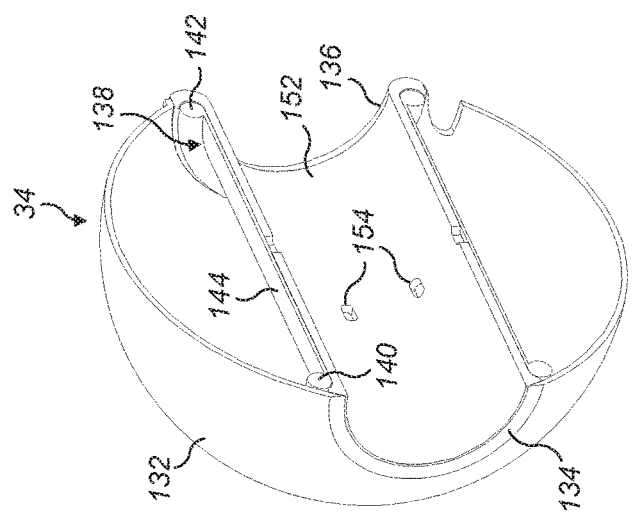
FIG. 12(c) is a similar view to FIG. 12(a) but with the diaphragm in an almost fully expanded configuration.

In this embodiment, the cleaning tool 14 comprises an expansion chamber 148 which is located adjacent to the inner wall 138. The expansion chamber 148 has a volume which increases as the volume of the fluid reservoir 34 decreases. In this embodiment, the expansion chamber 148 is open to the atmosphere to allow atmospheric air to enter the expansion chamber 148 as the inner wall 138 moves towards the external wall 132 as working fluid is supplied to the fluid delivery system 100. The expansion chamber 148 is shown in FIGS. 12(b) and 12(c), which illustrate the inner wall 138 in a partially expanded configuration, and in an almost fully expanded configuration, respectively. The expansion chamber 148 is delimited by the internal surface 146 of the inner wall 138, and the external surface 150 of an expansion chamber wall 152. The expansion chamber wall 152 is also generally tubular in shape, and is formed from relatively rigid material. The ends of the expansion chamber wall 152 are also connected to the ends of the external wall 132 and the inner wall 138 of the fluid reservoir 34 so that the expansion chamber wall 152 moves with the fluid reservoir 34 as the collar 124 is moved relative to the handle 12. The expansion chamber wall 152 is preferably in the form of a sleeve which extends around, and is moveable relative to, the outer wall of the stem 26. One or more apertures or ports 154 are formed in the expansion chamber wall 152 to allow atmospheric air to enter the expansion chamber 148, for example, from an air flow path which extends between the stem 26 and the expansion chamber wall 152, with expansion of the inner wall 138.

As the inner wall 138 expands towards its fully expanded configuration, the size and shape of the inner wall 138 approaches that of the external wall 132. In other words, when the inner wall is in a fully expanded configuration, which occurs when the fluid reservoir 34 is substantially empty, the size and the shape of the inner wall 138 are substantially the same as the size and the shape of the external wall 132 of the fluid reservoir 34. Thus, the maximum volume of the expansion chamber 148 is preferably substantially the same as the maximum volume of the fluid reservoir 34.

Figure 13A:
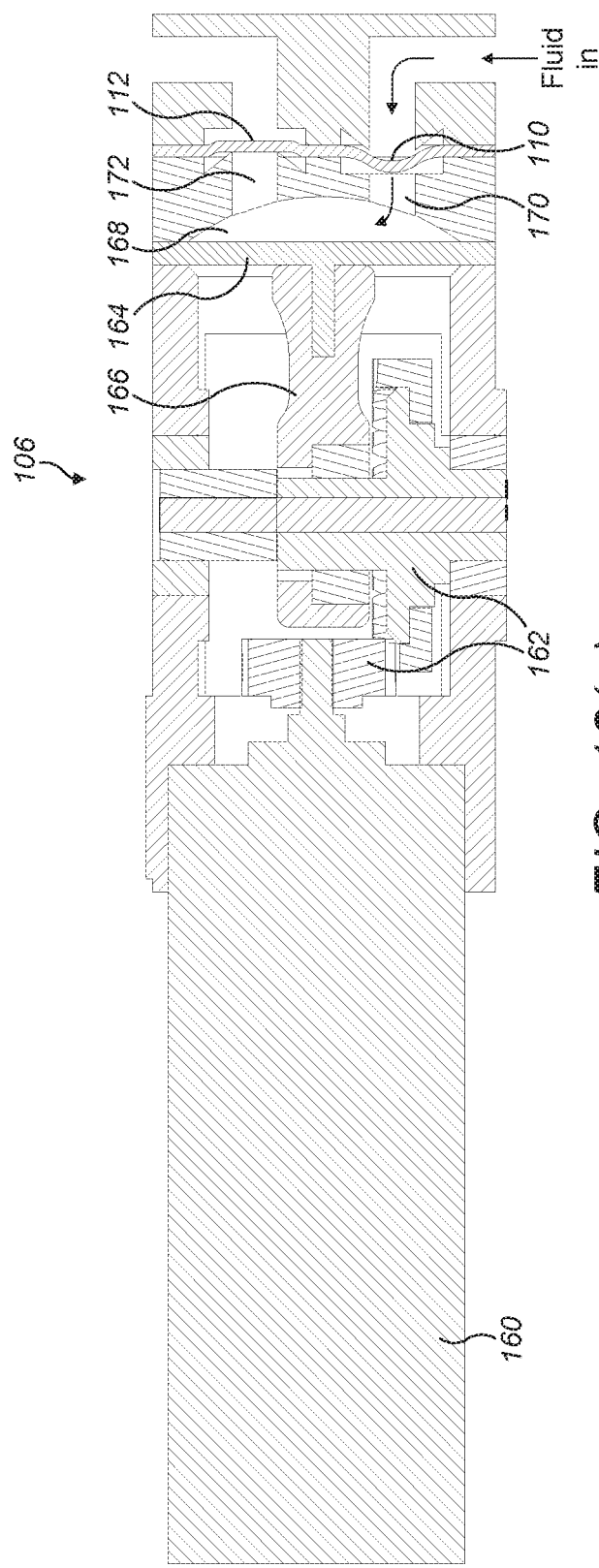
FIGS. 13(a) and 13(b) are sectional view of a diaphragm pump of the fluid delivery system, with the pump in intake and output configurations respectively.
Figure 13B:
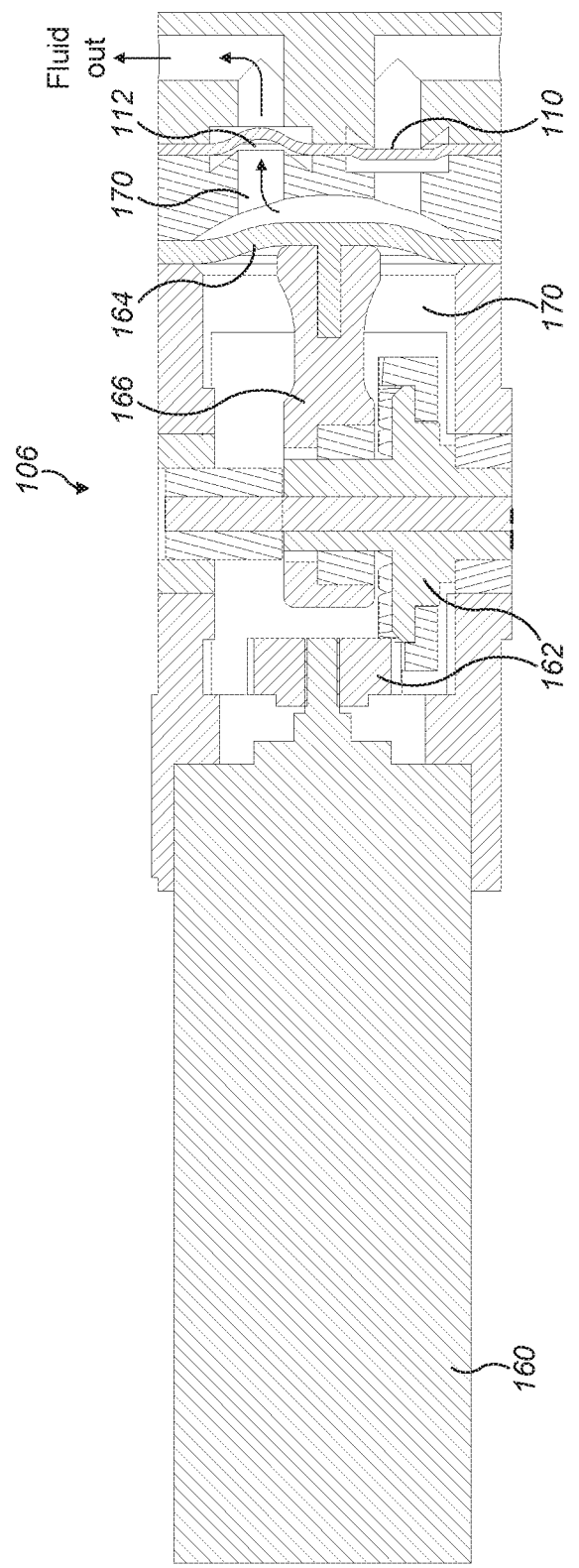

Working fluid is drawn from the fluid reservoir 34 by a pump 106 of the fluid delivery system 100. The pump 106 is fluidly connected to the fluid inlet 104 by a fluid conduit 156 of the handle fluid conduit system 116. The pump 106 is preferably in the form of a diaphragm pump, which incorporates the one-way valves 110, 112 of the fluid delivery system 100. With reference to FIGS. 13(*a*) and 13(*b*), the pump 106 comprises a motor 160 which is actuated by the control circuit 58. The motor 160 is also powered by the battery 60. The motor 160 drives a gear train 162 which is connected to the centre of a diaphragm 164 by a crank 166. The diaphragm 164 delimits a pump chamber 168 having a chamber inlet 170 and a chamber outlet 172. During activation of the motor 160, the diaphragm 164 moves between a first configuration, as shown in FIG. 13(*a*), and a second configuration, as shown in FIG. 13(*b*). As the diaphragm 164 moves towards the first configuration, the first one-way valve 110 is pulled into an open position, and the second one-way valve 112 is pulled into a closed position, as shown in FIG. 13(*a*). This allows working fluid to be drawn into the expanding pump chamber 166 through the chamber inlet 170. With subsequent movement of the diaphragm 164 towards the second configuration, the first one-way valve 110 is pushed into a closed position, and the second one-way valve 112 is pushed into an open position, as shown in FIG. 13(*b*). This allows working fluid to be pushed from the contracting pump chamber 166 through the chamber outlet 172.

With the second one-way valve 110 in an open position and the solenoid valve 114 in a closed position, working fluid is conveyed by fluid conduit 174 to the accumulator 108. A first embodiment of an accumulator 108 is illustrated in FIGS. 14(*a*) and 14(*b*), in which the accumulator 108 is in the form of a spring-type accumulator. The accumulator 108 comprises a fluid port 180 for receiving working fluid from the fluid conduit 174, and for conveying the received working fluid to a fluid chamber 182. The fluid chamber 182 is delimited by an elastic diaphragm 184 which is urged by a spring-loaded piston 186 towards the fluid port 180, and thus in a direction which urges working fluid from the fluid chamber 182 back through the fluid port 180. As working fluid enters the fluid chamber 182 from the pump 106, the diaphragm is urged, by the working fluid within the fluid chamber 182, away from the fluid port 180, as shown in FIG. 14(*b*), against the biasing force of the spring 188. A stop member may be provided for restricting the movement of the piston 186 away from the fluid port 180. The stop member may comprise a sensor which generates an output to the control circuit 58 upon contact with the piston 186. When the second one-way valve 112 is in a closed position, and with the solenoid valve 114 remaining in the closed position, a volume of working fluid is held under pressure within the fluid chamber 182.

An alternative, second embodiment of an accumulator 190 is illustrated in FIGS. 15(*a*) and 15(*b*), in which the accumulator 190 is in the form of a gas-charged accumulator. Similar to the accumulator 108, the accumulator 190 comprises a fluid port 192 for receiving working fluid from the fluid conduit 174, and for conveying the received working fluid to a fluid chamber 194. The fluid chamber 194 is delimited by an elastic diaphragm 196 which is urged by a gas-filled chamber 198 towards the fluid port 192, and thus in a direction which urges working fluid from the fluid chamber 194 back through the fluid port 192. As working fluid enters the fluid chamber 194 from the pump 106, the diaphragm is urged, by the working fluid within the fluid chamber 182, away from the fluid port 180, as shown in FIG. 15(*b*), against the biasing force exerted on the diaphragm 196 by the gas within the gas-filled chamber 198. When the second one-way valve 112 is in a closed position, and with the solenoid valve 114 remaining in the closed position, a volume of working fluid is held under pressure within the fluid chamber 194. Again, a stop member may be provided for restricting the movement of the diaphragm 196 away from the fluid port 192. The stop member may comprise a sensor which generates an output to the control circuit 58 upon contact with the diaphragm 196.

A sectional view of the solenoid valve 114 is illustrated in FIG. 16(*a*), and in exploded form in FIG. 16(*b*). The solenoid valve 114 comprises a core housing 200, which comprises a fluid inlet 202 of the solenoid valve 114, and a lower valve housing 204 which comprises a fluid outlet 206 of the solenoid valve 114. An O-ring 208 forms a seal between the core housing 200 and the lower valve housing 204. The lower valve housing 204 defines a valve seat 210 against which a core 212 is urged by a spring 214 located between the core housing 200 and the core 212. A coil 216 is located around the core housing 200, and a flux conductor 218 is located around the coil 216. The coil 216 is connected to the control circuit 58, which selectively energizes the coil 216 to generate a magnetic field which pulls the core 212 away from the valve seat 210, and so actuate a transition of the solenoid valve 114 from a closed position, as illustrated in FIG. 16(*a*), to an open position to allow working fluid to pass from the fluid inlet 202 to the fluid outlet 206. When the coil 216 is de-energised, the spring 214 urges the core 212 against the valve seat 210 to place the solenoid valve 214 in a closed position.

The fluid outlet 206 of the solenoid valve 114 is connected to the handle fluid outlet port 120 by fluid conduit 222. As illustrated in FIG. 4, the handle fluid outlet port 120 is located adjacent to the fluid inlet 104 on the end surface 42 of the body 16. The handle fluid outlet port 120 is also spaced from the longitudinal axis X of the handle 12, and in this embodiment is located diametrically opposite to the male connector 38. The handle fluid outlet port 120 is also angularly spaced from the drive unit coupling member 70. The cleaning tool 14 comprises a cleaning tool fluid inlet port 224 for receiving working fluid from the handle fluid outlet port 120. The cleaning tool fluid inlet port 224 is preferably in the form of a male connector which is received by the handle fluid outlet port 120. Alternatively, the cleaning tool fluid inlet port 224 may be in the form of a female connector, and the handle fluid outlet port 120 may be in the form of a male connector which is received by the cleaning tool fluid inlet port 224.

Figure 17A:
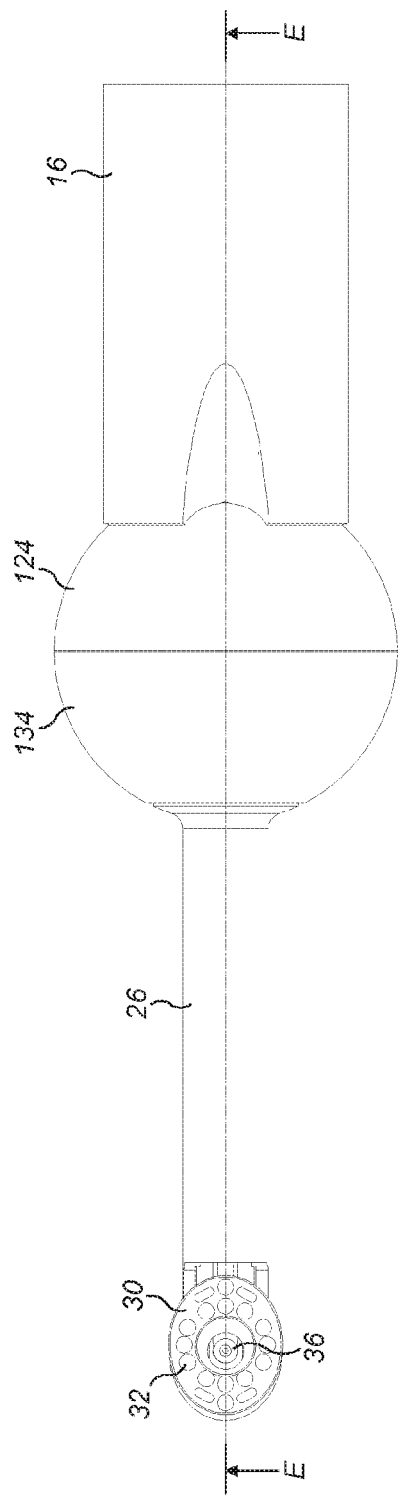
FIG. 17(a) is a front view of the cleaning tool and interfacing components of the body of the handle.
Figure 17B:
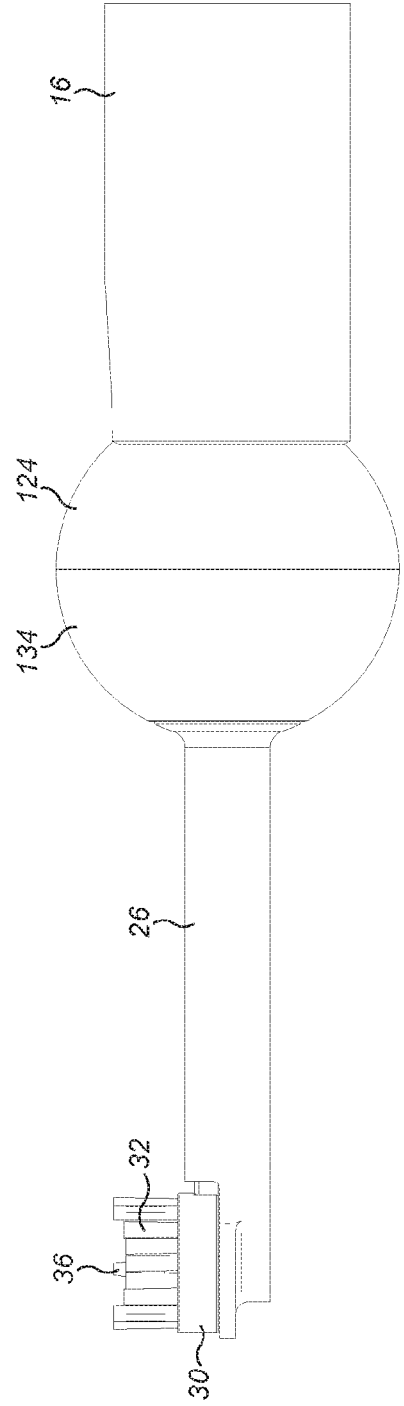
FIG. 17(b) is a right side view of the cleaning tool and interfacing components of the body of the handle.
Figure 17C:
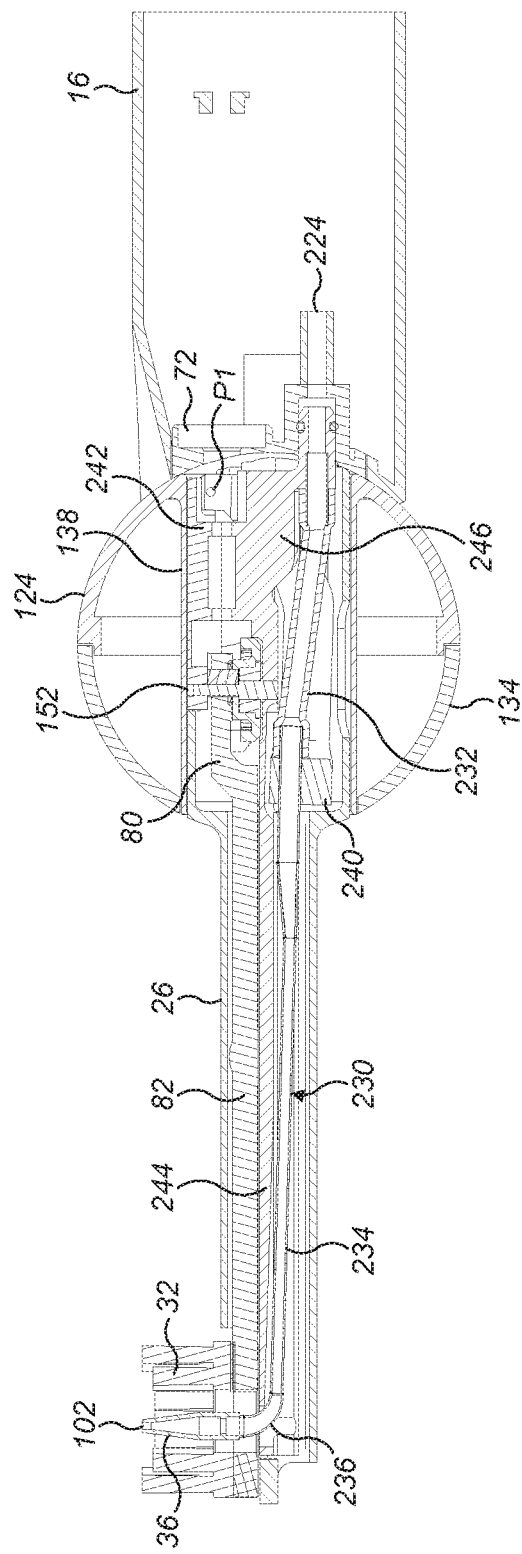
FIG. 17(c) is a side sectional view taken along line E-E in FIG. 17(a)
Figure 18A:
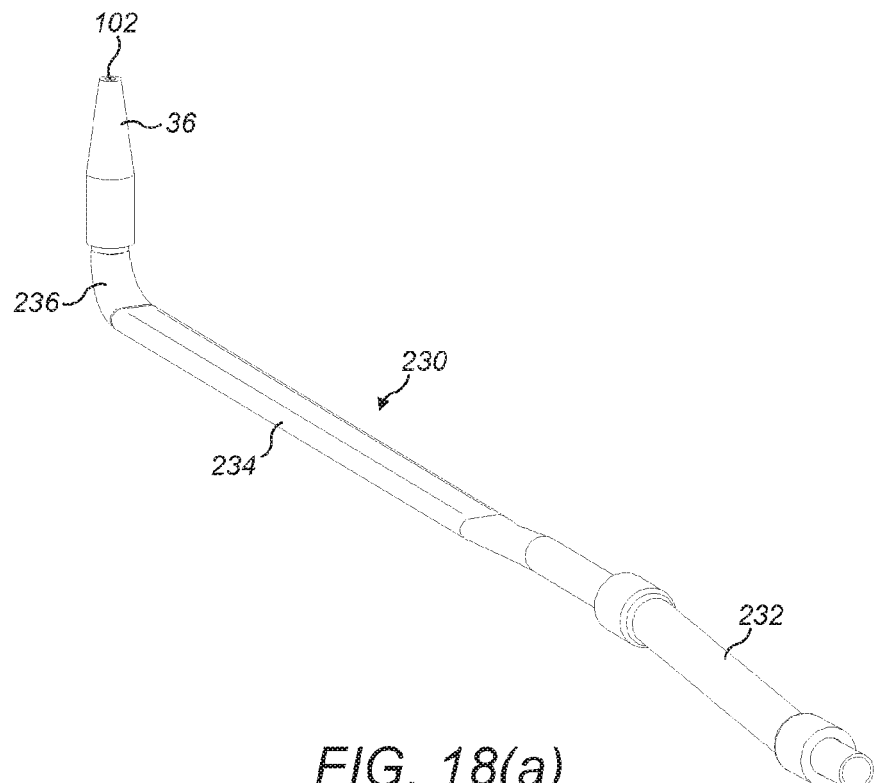
FIG. 18(a) is a perspective view of a cleaning tool conduit system.
Figure 18B:
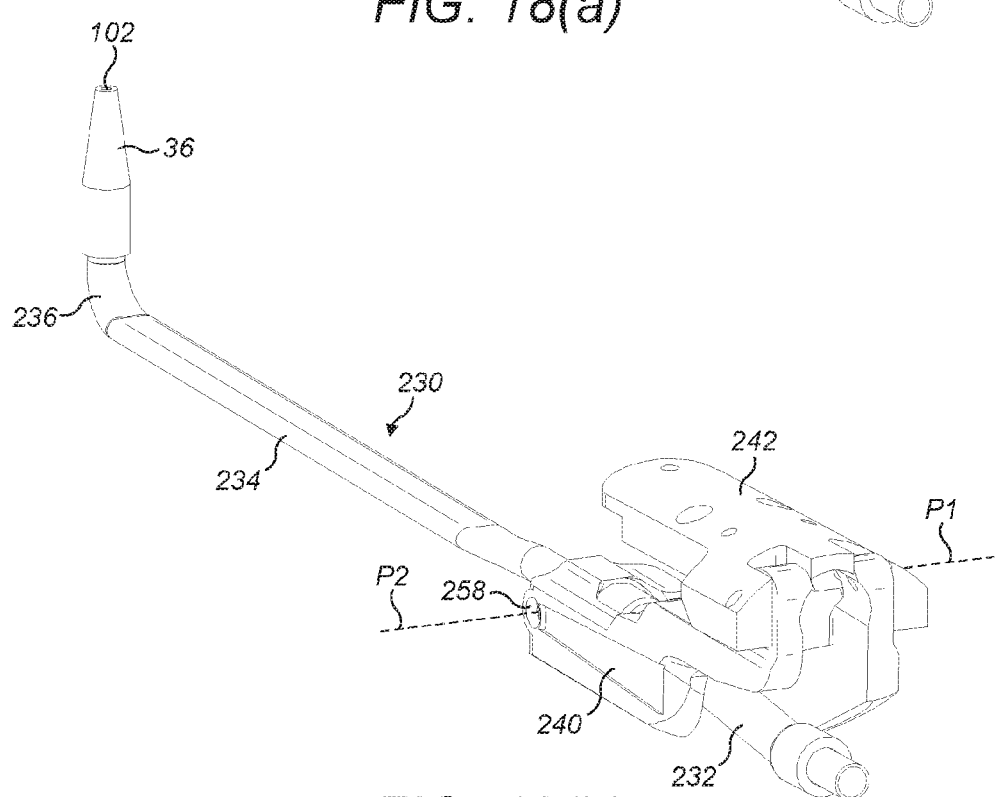
FIG. 18(b) is a similar view to FIG. 18(a) but with the addition of a pivotable support for a fluid conduit of the cleaning tool conduit system.
Figure 18C:
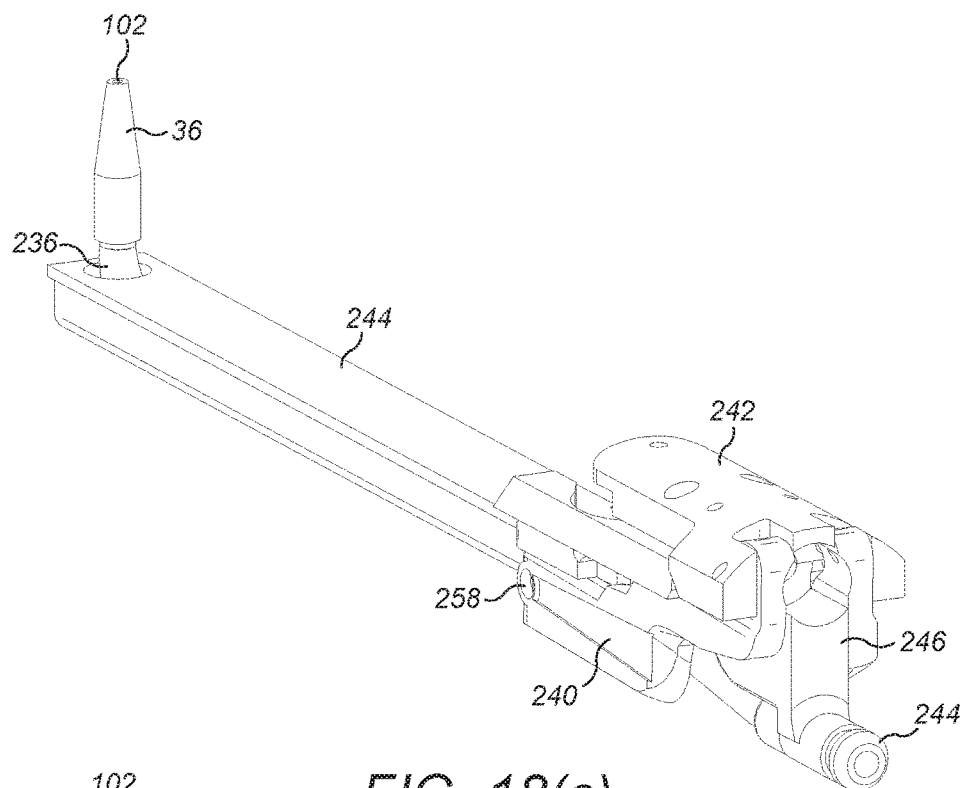
FIG. 18(c) is a similar view to FIG. 18(b) but with the addition of a static guide member.
Figure 18D:
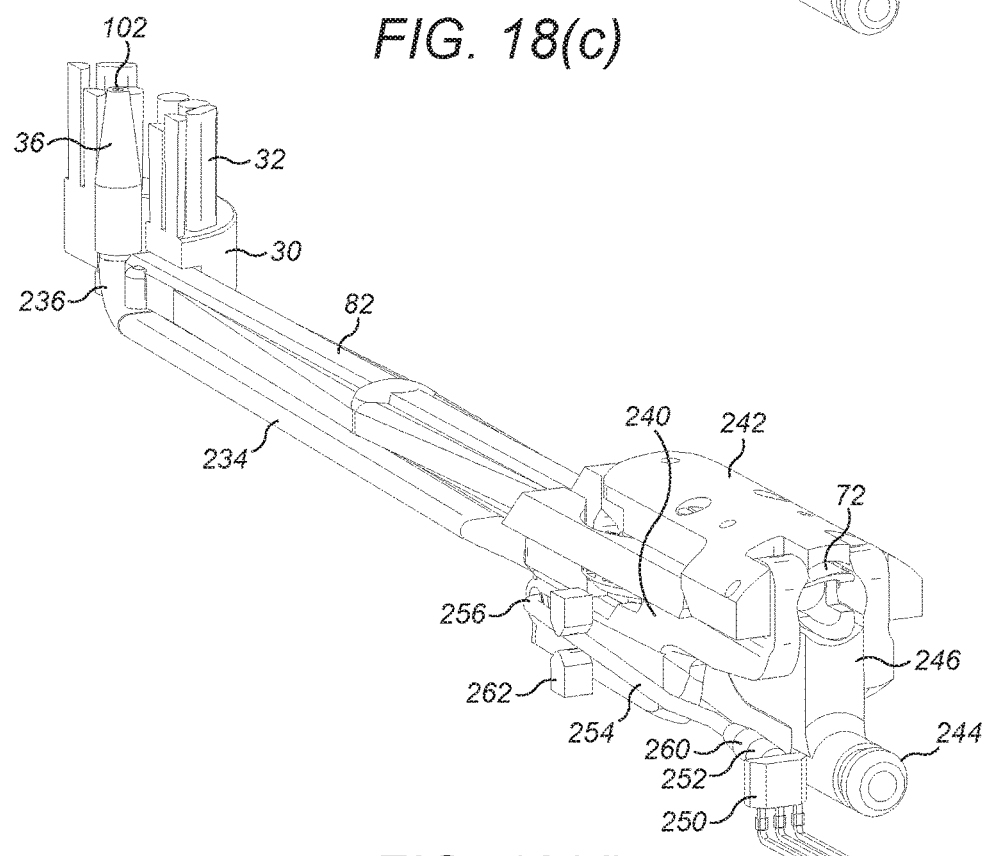
FIG. 18(d) is a similar view to FIG. 18(b) but with the addition of the transmission unit, part of the brush unit and a system for detecting motion of the support.

The cleaning tool fluid inlet port 224 provides a fluid inlet of the cleaning tool conduit system 118. The fluid outlet 102 of the nozzle 36 provides a fluid outlet of the cleaning tool conduit system 118. With reference to FIGS. 17 and 18, the cleaning tool conduit system 118 comprises a plurality of conduits for conveying working fluid from the cleaning tool fluid inlet port 224 to the nozzle 36. In this embodiment, the cleaning tool conduit system comprises a relatively rigid, first fluid conduit 230, preferably formed from plastics or metallic material, and relatively flexible, second fluid conduit 232, preferably formed from resilient elastic material, for example PVC.

The second fluid conduit 232 extends between the first fluid conduit 230 and the cleaning tool fluid inlet port 224. The first fluid conduit 230 comprises an elongate first section 234 which extends within the stem 26, adjacent to the connecting rod 82, and a second section 236. One end of the first section 234 is connected to the second fluid conduit 232, and the other end of the first section 234 is connected to the second section 236 of the first fluid conduit 230. The second section 236 is angled to the first section 234, and in this embodiment is in the formed of a curved conduit section which curves at an angle of around 90° to convey working fluid into the nozzle 36. The nozzle 36 is connected to the second section 236 of the first fluid conduit 230.

The first fluid conduit 230 is connected to a relatively rigid support 240. The support 240 is in turn connected to a support mount 242, which is held in a fixed position within, and relative to, the stem 26. The support 240 is movable relative to the support mount 242, and thus relative to the stem 26. In this embodiment, the support 240 is connected to the support mount 242 for pivoting movement about pivot axis P1. Pivot axis P1 passes through the stem 26, and is substantially orthogonal to the longitudinal axis Y of the cleaning tool 14.

The first fluid conduit 230 is thus pivotable relative to the stem 26 of the cleaning tool 14, and thus also pivotable relative to the handle 12. A guide member 244 is connected to the support mount 242 to guide the pivoting movement of the first fluid conduit 230 relative to the stem 26. In view of the connection of the nozzle 36 to the first fluid conduit 230, any movement of the first fluid conduit 230 relative to the stem 26 causes the nozzle 36 to move with the first fluid conduit 230. This, in turn, results in movement of the nozzle 36 relative to the brush unit 29 connected to the stem 26. In this embodiment, the first fluid conduit 230 is shaped so that pivoting movement of the first fluid conduit 230 about the pivot axis P1 causes the nozzle 36 to move relative to the brush unit 29 along a circular path which extends about the pivot axis P1.

The nozzle 36 is moveable relative to the brush unit 29 between a first, or distal, position relative to the brush unit 29, and a second, or proximal, position relative to the brush unit 29. In the distal position, the tip of the nozzle 36 protrudes outwardly beyond the ends of the bristles 32, whereas in the proximal position, the tip of the nozzle 36 is retracted relative to the ends of the bristles 32.

The guide member 244 may comprise stop members for inhibiting the movement of the nozzle 36 beyond the distal position, as shown in FIG. 19(a), and the proximal position, as shown in FIG. 19(b). The distance travelled by the tip of the nozzle 36 as the nozzle 36 moves from the distal position to the proximal position is preferably in the range from 1 to 5 mm, and in this embodiment is around 3 mm. When the nozzle 36 is in its distal position, the nozzle axis Z is preferably substantially orthogonal to the longitudinal axis Y of the cleaning tool 14. As the first fluid conduit 230 is pivotable about pivot axis P1, the tip of the nozzle 36 moves relative to the brush unit 29 in a circular path which has a centre which passes through the pivot axis P1. The angular movement of the tip of the nozzle 36 about the pivot axis P1 as the nozzle 36 moves from the distal position to the proximal position is preferably around 2.5°.

The first fluid conduit 230 is biased for movement about the pivot axis P1 in such a direction that urges the nozzle 36 towards the distal position relative to the brush unit 29. A separate biasing member may be located within the stem 26 for urging the first fluid conduit 230, or the support 240, to pivot in that direction relative to the pivot axis P1. In this embodiment, the first fluid conduit 230 is urged to move in that direction by the second fluid conduit 232. As mentioned above, the second fluid conduit 232 is preferably formed from resilient material, and so may be connected between the first fluid conduit 230 and the cleaning tool fluid inlet port 224 in an elastically deformed configuration. One end of the second fluid conduit 232 is held in a fixed position relative to the stem 26 by the cleaning tool fluid inlet port 224. The cleaning tool fluid inlet port 224 is, in turn, connected to the support mount 242 by a connector 246 to which the second contrate gear 76 is mounted for rotational movement relative thereto. The other end of the second fluid conduit 232, which is connected to the first fluid conduit 230, is free to move relative to the stem 26. The internal force created within the elastically deformed second fluid conduit 232 acts in such a direction as to urge that moveable end of the second fluid conduit 232 to move relative to the fixed end of the second fluid conduit 232. This in turn urges the first fluid conduit 230 to pivot in the aforementioned direction relative to the pivot axis P1 that urges the nozzle 36 towards the distal position relative to the brush unit 29.

A sensor 250 is provided for detecting movement of the support 240, and thus movement of the first fluid conduit 230 and the nozzle 36 which move with the support 240, relative to the handle 12 and the stem 26 of the cleaning tool 14. The sensor 250 is connected to the control circuit 58. In this embodiment, the sensor 250 is in the form of a Hall effect sensor which detects the movement of a magnet 252 connected to the support 240, and which generates an output having a voltage which is dependent on the relative positions of the sensor 250 and the magnet 252. The control circuit 58 is configured to receive the output from the sensor 250, and to sample that output every 10 ms, or at a frequency of 100 Hz, to generate a sampled output, or sampled voltage, S, every 10 ms.

From the sampled outputs received every 10 ms, the control circuit 58 is configured to generate the rate of change, Sr, of the sampled outputs from the difference between consecutive sampled outputs. Thus, the control circuit is configured to calculate a value for Sr every 10 ms.

The control circuit is further configured to determine an average rate of change of the sensor output, Sa, by calculating the average value of the 10 most recent values of Sr. A value for Sa is thus also calculated every 10 ms from the values of Sr calculated during the preceding 100 ms time period.

The magnet 252 is connected to an arm 254, which is in turn connected to the support 240. The arm 254 comprises a first end 256 which is inserted into a socket 258 formed in the support 240 so that the first end 256 of the arm 254 is rotatable within the socket 258. The magnet 252 is connected to the second end 260 of the arm 256. The length of the arm 256 is chosen so that the magnet 252 is located adjacent to the end surface of the cleaning tool 14 which faces the handle 12 when the cleaning tool 14 is connected to the handle 12. This can allow the sensor 250 to be located in the handle 12, and thus facilitate the connection of the sensor 250 to the control circuit 58.

The arm 254 is preferably pivotable relative to the support 240 about a second pivot axis P2. The second pivot axis P2 is spaced from, and substantially parallel to, the pivot axis P1. The second pivot axis P2 passes through the socket 258 into which the first end 256 of the arm 254 is connected so that a given movement of the first end 256 of the arm 254, through movement of the support 240 about the pivot axis P1, results in a greater movement of the second end 260 of the arm 254 about the second pivot axis P2. This serves to amplify the movement of the magnet 252 relative to the sensor 250, in comparison to the movement that would be produced were the magnet 252 connected directly to the support 240. The movement of the arm 256 about the second pivot axis P2 is guided by a pair of constraints 262 between which the arm 256 is located, and which are connected to the stem 26.

In use, the user first fills the fluid reservoir 34 with working fluid, which in this embodiment is water. As shown in FIG. 20, the user may place the appliance 10 beneath the spout of a tap and turn on the tap so that water from the spout enters the recessed portion 126 of the body 16 of the handle 12. With the collar 124 in the first position so that the fluid port 122 is exposed, the curved wall 128 guides water through the fluid port 122 and into the fluid reservoir 34. As the external wall 132 of the fluid reservoir 34 is transparent, the user can observe the filling of the fluid reservoir 34, and the contraction of the inner wall 138 of the fluid reservoir 34 under the weight of the water within the fluid reservoir 34. As the fluid reservoir 34 becomes filled with water, air is expelled from the expansion chamber 148. When the fluid reservoir 34 is full, the user moves the collar 124 to the second position to connect the fluid port 122 to the fluid inlet 104 of the fluid delivery system 100.

The user switches on the appliance 10 by depressing button 22, the action of which is detected by the control circuit 58. The user can then select a mode of operation of the appliance 10 by depressing button 20. The currently selected mode of operation of the appliance 10 is displayed on the display 24, and the user can toggle between the various selectable modes of operation by depressing button 20 until the desired operational mode is displayed on the display 24. In this embodiment, there are six different user selectable operational modes:

| MODE | BRUSHING | MANUAL JET | AUTO JET |
|---|---|---|---|
| 1 | ON | OFF | OFF |
| 2 | ON | ON | OFF |
| 3 | ON | OFF | ON |
| 4 | OFF | ON | OFF |
| 5 | OFF | OFF | ON |
| 6 | ON | ON | ON |

When any of modes 1 to 3 or 6 are selected, the control circuit 58 activates the motor 56 to move the brush unit 29 relative to the handle 12 to brush teeth 300, shown in FIG. 21, against which the brush unit 29 is pressed by the user. The drive mechanism 50 and the motor 58 are configured to generate a movement of the bristle carrier 30 about the nozzle 36 in the range from 4,000 to 6,000 revolutions per minute, where each revolution is a single 360° rotation of the crank 78, and thus a single 360° orbital movement of the bristle carrier 30 about the nozzle 36.

When any of modes 2 to 6 are selected, initially the control circuit 58 operates the pump 106 to charge the accumulator 108. With the solenoid valve 114 in a closed position, the pump 106 is operated for a period of time, in this embodiment around 500 ms, to draw a volume of water from the fluid reservoir 34, and to convey that volume of drawn water to the accumulator 108. In this embodiment, the volume of water which is drawn from the fluid reservoir 34 each period of time that the pump 106 is operated is around 0.25 ml. When that volume of water is received by the accumulator 108, the pressure of water within the fluid chamber 182 of the accumulator 108 is around 5.5 bar (around 550 kPa). The pump 106 may be deactivated by the control circuit 58 upon expiry of that period of time, or in response to the receipt of an output generated by the sensor located in the accumulator 108. Following delivery of that volume of water to the accumulator 108, the second one-way valve 112 is in a closed position to prevent water from returning to the pump 106 from the accumulator 108.

When mode 2, mode 4 or mode 6 is selected by the user, a burst of water is emitted from the nozzle 36 in response to user depression of the button 18. The depression of the button 18 is detected by the control circuit 58. The control circuit 58 activates the coil 216 of the solenoid valve 114 to move the solenoid valve 114 to the open position. This allows the piston 186 of the accumulator 108 to move rapidly towards the fluid port 180 to urge the volume of water out from the accumulator 108 in the form of a pressurised burst of water. The time taken to urge that volume of water from the accumulator 108 is preferably in the range from 1 to 50 ms, and in this embodiment is around 30 ms. The burst of water passes though the solenoid valve 114 and the cleaning tool conduit system 118 to be ejected from the fluid outlet of the nozzle 36. When the nozzle 36 is positioned within or aligned with an interproximal gap, the burst of water ejected from the nozzle 36 can dislodge matter located within the interproximal gap.

The control circuit 58 is arranged to replenish the accumulator 108 following the delivery of the burst of water to the cleaning tool conduit system 118. The control circuit 58 is arranged to move the solenoid valve 114 to the closed position, and to operate the pump 106 to convey another volume of water from the fluid reservoir 34 to the accumulator 108. The control circuit 58 is configured to disable the opening of the solenoid valve 114, in response to the user depression of the button 18, until the accumulator 108 has become fully replenished with water, and so for a period of around 500 ms after the last burst of water was ejected from the nozzle 36.

When mode 3, mode 5 or mode 6 is selected by the user, a burst of water is emitted from the nozzle 36 depending on an output from the sensor 250. Thus, when mode 6 is selected, a burst of water is emitted from the nozzle 36 depending on an output from the sensor 250 or in response to user depression of the button 18. FIGS. 21(a) to 21(f) illustrate schematically the use of the appliance 10 to clean a user's teeth 300. As the brush unit 29 is moved across the user's teeth, the tip of the nozzle 36 engages the user's teeth. The force that is applied to the nozzle 36 as the nozzle 36 is pushed against the user's teeth overcomes the biasing force applied to the first fluid conduit 230 by the second fluid conduit 232, and so the nozzle 36 moves away from the distal position towards its proximal position. As the brush unit 29 is moved across, for example, tooth 302, the position of the nozzle 36 relative to the stem 26 will vary depending on the contours of the tooth 302 and the force with which the head 28 is pressed against the tooth 302.

Figure 21A:
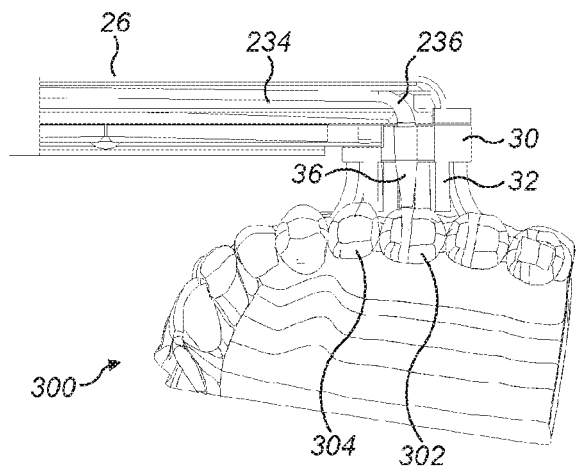
FIGS. 21(a) to (f) illustrate schematically the movement of the cleaning tool over a user's teeth and the ejection of working fluid into an interproximal gap.
Figure 21B:
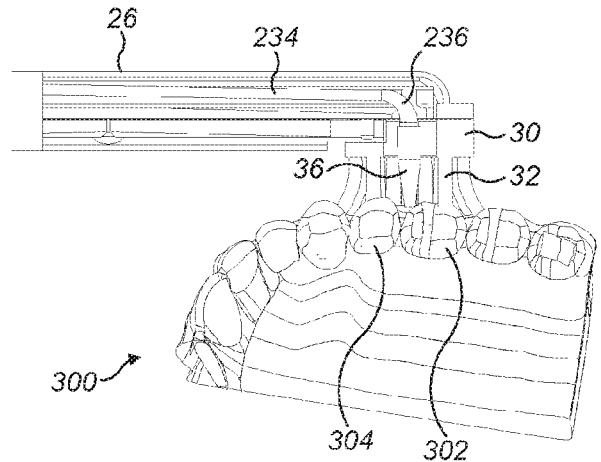
Figure 21C:
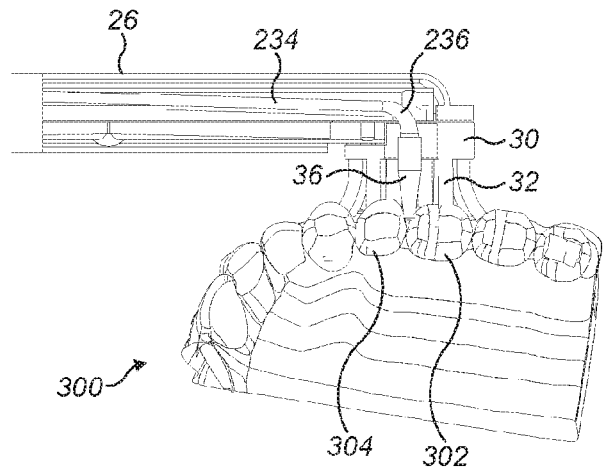
Figure 21D:
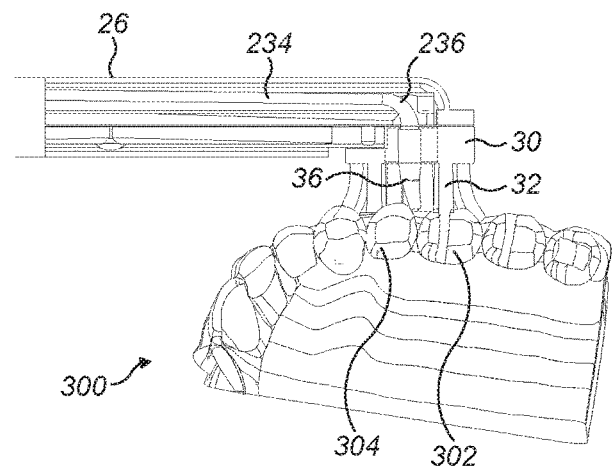
Figure 21E:
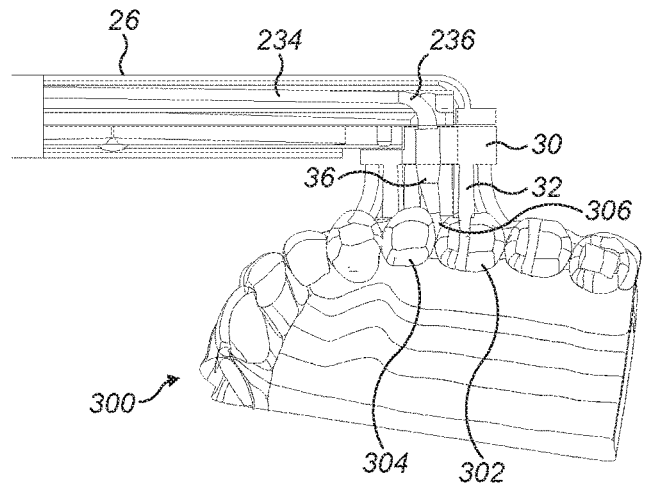
Figure 21F:
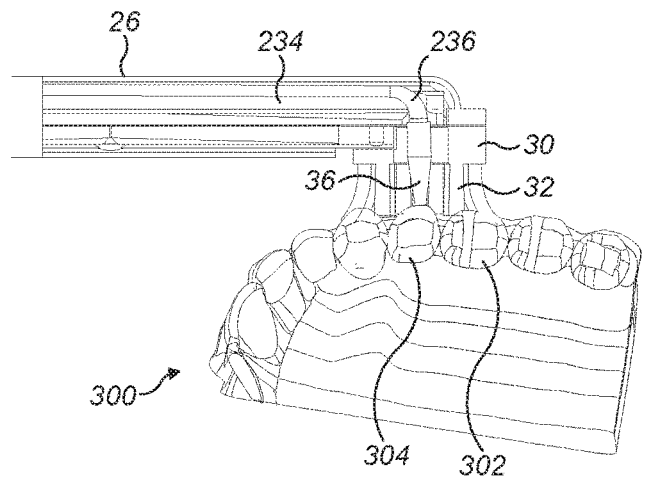

The control circuit 58 is initially in a first, or "unprimed", condition. As the brush unit 29 passes from tooth 302 to the adjacent tooth 304, the nozzle 306 becomes positioned over the interproximal gap between those teeth, as shown in FIG. 21(c). In that position, the force acting on the nozzle 36, through its engagement with the teeth of the user, is removed. This allows the second fluid conduit 232 to urge the first fluid conduit 230 to pivot about the pivot axis P1, which moves the nozzle 36 rapidly towards its distal position. This movement of the first fluid conduit 230 about the pivot axis P1 causes the support 240 to move relative to the support mount 242, which in turn causes the magnet 252 to move rapidly, relative to the sensor 250, towards the position shown in FIG. 19(a).

This generates a rapid variation in the signal output from the sensor 250 to the control circuit 58, and thus a relatively large change in the value of Sa calculated by the control circuit 58. In this embodiment, Sa has a relatively large negative value when the nozzle 36 moves rapidly towards its distal position. When the value of Sa falls below a first threshold value, which occurs when the tip of the nozzle 36 enters an interproximal gap, the control circuit 58 enters a second, or "primed", condition.

With the tip of the nozzle 36 now located within the interproximal gap, the value of Sa increases rapidly. This can be to a value of approximately zero, or to a value greater than zero as the nozzle 36 moves away its distal position as the tip of the nozzle 36 begins to move over the tooth 304.

When the value of Sa subsequently rises above a second threshold value, which is greater than the first threshold value, the control circuit 58 enters a third, or "ejection", condition, in which the control circuit 58 activates the coil 216 of the solenoid valve 114 to open the solenoid valve 114. As described above, the opening of the solenoid valve 114 causes a burst of water, as identified at 306 in FIG. 21(e), to be ejected from the nozzle 36 into the interproximal gap between the teeth.

Following the delivery of the burst of water to the cleaning tool conduit system 118, the control circuit 58 is arranged to replenish the accumulator 108. The control circuit 58 is arranged to move the solenoid valve 114 to the closed position, and to operate the pump 106 to convey another volume of water from the fluid reservoir 34 to the accumulator 108. The control circuit 58 is configured to disable the opening of the solenoid valve 114 in response to the output received from the sensor 250, until the accumulator 108 has become fully replenished with water, and so for a period of around 500 ms after the last burst of water was ejected from the nozzle 36. Once the accumulator 108 has been replenished, the control circuit 58 returns to its first, or "unprimed", condition.

The appliance 10 may be configured to reduce the risk of undesired ejection of bursts of working fluid when the nozzle 36 is not located within an interproximal gap of the user, for example during handling of the appliance 10, when any of mode 2, mode 3 or mode 6 has been selected by the user. In each of these modes, the motor 56 is activated to move the bristle carrier 30 relative to the handle 12. To maintain a constant speed of movement of the bristle carrier 30 relative to the handle 12, the motor 56 may draw a variable amount of current, the magnitude of the drawn current varying as a resistance is applied to the motion of the brush unit 29 about the nozzle 36. The magnitude of the current drawn by the motor 56 can thus provide an indication that the brush head 29 is being pressed against a user's teeth.

The control circuit 58 may be configured to monitor the current which is drawn by the motor 56. When the current drawn by the motor 56 is below a pre-set threshold value, this can provide an indication that the brush unit 29 is not being used to clean a user's teeth, for example, when the appliance 10 has first been switched on by the user, or if the fluid reservoir 34 is being replenished by the user while the appliance 10 is switched on. In this event, the appliance 10 enters a first operational mode, in which the delivery of a burst of water to the teeth of a user is inhibited, irrespective of whether the button 18 is depressed (in mode 2 or mode 6) or the output from the sensor 250 (in mode 3 or mode 6).

When the current drawn by the motor 56 is above the pre-set threshold value, this can provide an indication that the brush unit 29 is being used to clean a user's teeth. In this event, the appliance 10 enters a second operational mode, in which the delivery of a burst of water to the teeth of a user is permitted. The current drawn by the motor 56 is continuously monitored by the control circuit 58, and the control circuit 58 is arranged to effect a transition between the first operational mode and the second operational mode automatically as the detected current falls below, or rises above, the threshold value.

A second, higher, threshold value may also be pre-set in the control circuit 58. When the current drawn by the motor 56 exceeds this second threshold value, the control circuit 58 may generate an alert, for example, an audible alert or a visual alert displayed on the display 24, to warn the user that the brush unit 29 is being pressed too firmly against the user's teeth.

In the above embodiment, the capacity of the fluid chamber 182 of the accumulator 108 is substantially the same as the volume of a single burst of working fluid. However, the capacity of the fluid chamber 182 may be larger than the volume of a single burst of working fluid.

In a second embodiment, the fluid chamber has a capacity of 0.75 ml, and a single burst of working fluid has a volume of around 0.25 ml. In this second embodiment, when in its third condition the control circuit 58 is arranged to hold the solenoid valve 114 in an open position for a time period which allows only the required volume of working fluid to be ejected from the accumulator 108 to form a single burst of working fluid. For example, the solenoid valve 114 may be held in an open position for a time period of 30 ms to allow a single burst of working fluid having a volume of 0.25 ml to be delivered to the nozzle 36. The control circuit 58 returns to its first condition following the ejection of that single burst of working fluid. In this case, and provided that there is sufficient working fluid in the accumulator 108 to deliver those three bursts of working fluid to the nozzle 36, the control circuit 58 is arranged to replenish the accumulator 108 following the delivery of every third burst of working fluid to the cleaning tool conduit system 118.

In a third embodiment, the fluid chamber has a capacity of 0.25 ml, and a single burst of working fluid has a volume of around 0.08 ml. Similar to the second embodiment, in this third embodiment the control circuit 58 is arranged to hold the solenoid valve 114 in an open position for a time period which allows only the required volume of working fluid to be ejected from the accumulator 108 to form a single burst of working fluid. For example, the solenoid valve may be held in an open position for a time period of around 10 ms to allow a single burst of working fluid having a volume of 0.08 ml to be delivered to the nozzle 36. Again, in this case the control circuit 58 is arranged to replenish the accumulator 108 following the delivery of every third burst of working fluid to the cleaning tool conduit system 118, but the time required to replenish the accumulator 108 in this third embodiment is shorter than the time required to replenish the accumulator 108 in the second embodiment.

In each of the first to third embodiments, the control circuit 58 is arranged to deliver a single burst of working fluid depending on a received input, which is either an output from the sensor 250, or a user action on the appliance 10, such as the depression of the button 18. However, the control circuit 58 may be arranged to deliver a series of bursts of working fluid depending on such a received input. Each of the bursts of working fluid within a series preferably contains substantially the same volume of working fluid.

In a fourth embodiment, the fluid chamber 182 of the accumulator 108 has a capacity of 0.25 ml, and the control circuit 58 is arranged to control the fluid delivery system 100 to deliver a single series of three bursts of working fluid, each having a volume of around 0.08 ml, in response to user depression of the button 18, or depending on the output from the sensor 250, depending on whichever one of modes 2 to 6 has been selected by the user.

For example, when either mode 2 or mode 4 is selected by the user a series of bursts of water is emitted from the nozzle 36 in response to user depression of the button 18. The depression of the button 18 is detected by the control circuit 58. The control circuit 58 activates the coil 216 of the solenoid valve 114 to move the solenoid valve 114 to the open position. The control circuit 58 holds the solenoid valve 114 in the open position only for a time period which allows the piston 186 of the accumulator 108 to urge a volume of water from the accumulator 108 to form the first pressurised burst of water. In this embodiment, the time taken to urge that volume of water from the accumulator 108 is around 10 ms, and so after that period of time the control circuit 58 deactivates the coil 216 of the solenoid valve 114 to allow the solenoid valve 114 to move to the closed position.

Once the solenoid valve 114 is in the closed position, the control circuit 58 re-activates the coil 216 of the solenoid valve 114 to move the solenoid valve 114 back to the open position. Again, the control circuit 58 holds the solenoid valve 114 in the open position only for a time period which allows the piston 186 of the accumulator 108 to urge a second volume of water from the accumulator 108 to form the second pressurised burst of water, and so in this embodiment a second time period of around 10 ms.

After that period of time has elapsed, the control circuit 58 deactivates the coil 216 of the solenoid valve 114 to allow the solenoid valve 114 to move to the closed position. Once the solenoid valve 114 is in the closed position, the control circuit 58 again re-activates the coil 216 of the solenoid valve 114 to move the solenoid valve 114 back to the open position. Once again, the control circuit 58 holds the solenoid valve 114 in the open position only for a time period which allows the piston 186 of the accumulator 108 to urge a third volume of water from the accumulator 108 to form the third pressurised burst of water, and so in this embodiment a third time period of around 10 ms. After that period of time has elapsed, the control circuit 58 deactivates the coil 216 of the solenoid valve 114 to allow the solenoid valve 114 to move to the closed position. The pump 106 is then operated to replenish the accumulator 108.

Within a series, the time period between successive bursts of working fluid is preferably equal, and is preferably in the range from 1 to 25 ms, more preferably in the range from 2 to 10 ms, so that the entire series of bursts may be delivered to a single interproximal gap. This can allow for a slight variation in the position of the tip of the nozzle 36 relative to interproximal gap with each successive burst, and so potentially improving the removal of material from within the interproximal gap.

In this fourth embodiment, the capacity of the fluid chamber 182 of the accumulator 108 is substantially the same as the volume of working fluid which is ejected from the nozzle 36 in a single series of bursts of working fluid. Alternatively, the capacity of the fluid chamber 182 of the accumulator 108 may be greater than the volume of working fluid which is ejected from the nozzle 36 in a single series of bursts of working fluid. For example, in a fifth embodiment, the capacity of the fluid chamber 182 is increased to 0.75 ml, but the control circuit 58 is arranged to eject the same, single series of three bursts of working fluid, each having a volume of around 0.08 ml, in response to user depression of the button 18, or depending on the output from the sensor 250. Therefore, in this fifth embodiment the accumulator 108 requires replenishment following the delivery of three series of bursts of working fluid from the appliance 10.

The invention claimed is:

1. A dental cleaning appliance comprising:
   a handle; and
   a cleaning tool detachably connected to the handle, the cleaning tool comprising a nozzle for delivering a burst of working fluid to the teeth of a user, a stem extending between the handle and the nozzle, and a fluid reservoir for storing working fluid, the fluid reservoir being connected to and extending around the stem,
   wherein the fluid reservoir comprises an external wall that surrounds the stem and an inner wall that is connected to the external wall, the inner wall comprising a moveable member that is moveable relative to the external wall to vary the volume of fluid held between the external wall and the inner wall.

2. The appliance of claim 1, wherein the fluid reservoir is configured to store a liquid working fluid.

3. The appliance of claim 1, wherein the fluid reservoir has a capacity which is in the range from 5 to 50 ml.

4. The appliance of claim 1, wherein the fluid reservoir is refillable.

5. The appliance of claim 1, wherein at least part of the external wall is transparent.

6. The appliance of claim 1, wherein the external wall has one of a curved shape, a convex shape, and a faceted shape.

7. The appliance of claim 6, wherein the external wall has a curvature which is one of ellipsoidal, spheroidal and spherical.

8. The appliance of claim 1, wherein the external wall comprises a fluid port through which the fluid reservoir is replenished.

9. The appliance of claim 1, wherein the inner wall is tubular in shape.

10. The appliance of claim 1, wherein the cleaning tool comprises a head from which the nozzle protrudes, and the nozzle is moveable relative to the head between a distal position and a proximal position.

11. The appliance of claim 10, wherein the nozzle is biased towards the distal position.

12. The appliance of claim 10, wherein the head comprises one or more engagements for engaging the teeth of the user during use of the appliance, and wherein the nozzle is moveable relative to the one or more engagements.

13. The appliance of claim 12, wherein, when the nozzle is in the distal position, the tip of the nozzle protrudes beyond at least some of the one or more engagements.

14. The appliance of claim 12, wherein the one or more engagements are formed from resilient material.

15. The appliance of claim 14, wherein the one or more engagements comprises a plurality of resilient members arranged around the nozzle.

16. The appliance of claim 14, wherein the one or more engagements comprises a plurality of bristles arranged about the nozzle.

17. The appliance of claim 16, wherein the bristles are mounted on a bristle carrier which is moveable relative to the nozzle.

18. A cleaning tool for a dental cleaning appliance comprising a handle to which the cleaning tool is detachably connectable, the cleaning tool comprising:
   a stem;
   a nozzle for delivering the burst of working fluid to the teeth of a user; and
   a fluid reservoir for storing working fluid, the fluid reservoir being connected to and extending around the stem,
   wherein the fluid reservoir comprises an external wall that surrounds the stem and an inner wall that is connected to the external wall, the inner wall comprising a moveable member that is moveable relative to the external wall to vary the volume of fluid held between the external wall and the inner wall.

19. The cleaning tool of claim 18, wherein the fluid reservoir is configured to store a liquid working fluid.

20. The cleaning tool of claim 18, wherein the fluid reservoir has a capacity which is in the range from 5 to 50 ml.

21. The cleaning tool of claim 18, wherein the fluid reservoir is refillable.

22. The cleaning tool of claim 18, wherein at least part of the external wall is transparent.

23. The cleaning tool of claim 18, wherein the external wall has one of a curved shape, a convex shape, and a faceted shape.

24. The cleaning tool of claim 23, wherein the external wall has a curvature which is one of ellipsoidal, spheroidal and spherical.

25. The cleaning tool of claim 18, wherein the external wall comprises a fluid port through which the fluid reservoir is replenished.

26. The cleaning tool of claim 18, wherein the inner wall is tubular in shape.

27. The cleaning tool of claim 18, comprising a head from which the nozzle protrudes, wherein the nozzle is moveable relative to the head between a distal position and a proximal position.

28. The cleaning tool of claim 27, wherein the nozzle is biased towards the distal position.

29. The cleaning tool of claim 27, wherein the head comprises one or more engagements for engaging the teeth of the user during use of the appliance, and wherein the nozzle is moveable relative to the engagements.

30. The cleaning tool of claim 29, wherein, when the nozzle is in the distal position, the tip of the nozzle protrudes beyond at least some of the one or more engagements.

31. The cleaning tool of claim 29, wherein the one or more engagements is formed from resilient material.

32. The cleaning tool of claim 31, wherein the one or more engagements comprises a plurality of resilient members arranged around the nozzle.

33. The cleaning tool of claim 31, wherein the one or more engagements comprise a plurality of bristles arranged about the nozzle.

34. The cleaning tool of claim 33, wherein the bristles are mounted on a bristle carrier which is moveable relative to the nozzle.

35. The cleaning tool of claim 34, comprising a connecting rod connected to the bristle carrier, and a set of gears connected to the connecting rod.

\* \* \* \* \*